US010047343B2

(12) United States Patent
Kuo

(10) Patent No.: US 10,047,343 B2
(45) Date of Patent: Aug. 14, 2018

(54) METHODS FOR PRODUCING CARTILAGE AND BONE

(71) Applicant: Alfred Kuo, San Francisco, CA (US)

(72) Inventor: Alfred Kuo, San Francisco, CA (US)

( * ) Notice: Subject to any disclaimer, the term of this patent is extended or adjusted under 35 U.S.C. 154(b) by 190 days.

(21) Appl. No.: 14/599,324

(22) Filed: Jan. 16, 2015

(65) Prior Publication Data
US 2015/0175968 A1    Jun. 25, 2015

Related U.S. Application Data

(63) Continuation of application No. PCT/US2013/051022, filed on Jul. 18, 2013.

(60) Provisional application No. 61/673,903, filed on Jul. 20, 2012.

(51) Int. Cl.
C12N 5/077 (2010.01)
A61K 35/32 (2015.01)
A61K 35/00 (2006.01)

(52) U.S. Cl.
CPC ............ C12N 5/0655 (2013.01); A61K 35/32 (2013.01); A61K 35/00 (2013.01); C12N 2500/90 (2013.01); C12N 2501/15 (2013.01); C12N 2501/155 (2013.01); C12N 2501/37 (2013.01)

(58) Field of Classification Search
CPC .............. A61K 35/00; A61K 2500/90; C12N 2501/15; C12N 2501/155; C12N 2501/37; C12N 5/0655
See application file for complete search history.

(56) References Cited

U.S. PATENT DOCUMENTS

| 5,700,774 | A | * | 12/1997 | Hattersley ............... A61K 38/29 514/11.8 |
| 5,846,931 | A | | 12/1998 | Hattersley et al. |
| 6,150,163 | A | | 11/2000 | McPherson et al. |
| 6,258,778 | B1 | * | 7/2001 | Rodgers ............. A61K 38/1841 424/185.1 |
| 7,169,610 | B2 | | 1/2007 | Brown |
| 8,017,394 | B2 | | 9/2011 | Adkisson et al. |
| 8,142,808 | B2 | | 3/2012 | Boyan et al. |
| 2003/0175257 | A1 | | 9/2003 | Song et al. |
| 2006/0148077 | A1 | | 7/2006 | Thies |
| 2011/0256109 | A1 | | 4/2011 | Noble et al. |
| 2011/0159070 | A1 | * | 6/2011 | Jin ........................ A61L 27/06 424/423 |

FOREIGN PATENT DOCUMENTS

| EP | 13819300 | 2/2015 | |
| EP | 13819300.8 | 4/2016 | |
| WO | WO 9533830 A1 * | 12/1995 | ......... A61K 38/1875 |
| WO | WO 2004016151 A2 * | 2/2004 | ............ A61K 38/29 |
| WO | WO 2006135027 A1 * | 12/2006 | ......... A61K 38/1825 |
| WO | PCT/US2013/051022 | 10/2013 | |
| WO | WO 2014/015109 | 1/2014 | |

OTHER PUBLICATIONS

Madle, E; Van Der Veen, S; Verhaar, Jan; Van Osch, G "Serum-Free Medium Supplemented with High-Concentration FGF2 for Cell Expansion Culture of Human Ear Chondrocytes Promotes Redifferentiation Capacity" Tissue Engineering,2002,8(4),pp. 573-580.*
Shum et al, "BMP4 promotes chondrocyte proliferation and hypertrophy in the endochondral cranial base." Int J Dev Biol. Sep. 2003;47(6):423-31.*
Patil et al "An Update on Transforming Growth Factor-b (TGF-b): Sources, Types, Functions and Clinical Applicability for Cartilage/ bone Healing", J. Cell. Physiol. 226: 3094-3103, 2011.*
Brittberg, et al. Treatment of Deep Cartilage Defects in the Knee with Autologous Chondrocyte Transplantation. Eng J Med. 331(14):889-895 (1994).
Fischer, et al. Human Articular Chondrocytes Secrete Parathyroid Hormone—Related Protein and Inhibit Hypertrophy of Mesenchymal Stern Cells in Coculture During Chondrogenesis. Arthritis and Rheumatism. 62 (9): 2696-2706 (2010).
Gawlitta, et al. Modulating Endochondral Ossification of Multipotent Stromal Cells for Bone Regeneration. Tissue Engineering. 16(4): 385-395.
Iwata, et al. The development of a serum-free medium utilizing the interaction between growth factors and biomaterials. Biomaterials. 33: 444-454 (2012).
Jiang, et al. The Inductive Effect of Bone Morphogenetic Protein-4 on Chondral-Lineage Differentiation and In Situ Cartilage Repair. Tissue Engineering. 16(5): 1621-1632 (2010).
Johnstone, B., et al. In vitro chondrogenesis of bone marrow-derived mesenchymal progenitor cells. Exper. Cell Res. 238(1): 265-272 (1998).
Jukes, et al. Endochondral bone tissue engineering using embryonic stem cells, Proc. Natl. Acad. Sci. USA. 105(19): 6840-6845 (2008).
Lee, J. and Im, G. PTHrP isoforms have differing effect of chondrogenic differentiation and hypertrophy of mesenchymal stern cells. Biochem. Biophys. Res. Comm. 421(4): 819-824 (2012).
Liu, G., et al. Optimal combination of soluble factors for tissue engineering of permanent cartilage from cultured human chondrocytes. Journ. Biol. Chem. 282(28): 20407-20415 (2007).
Melhorn, A.T., et al. Differential effects of BMP-2 and TGF-beta1 on chondrogenic differentiation of adipose derived stem cells. Cell Prolif. 40(6): 809-823 (2007).

(Continued)

Primary Examiner — Christopher Robin Tate
Assistant Examiner — Aaron J Kosar
(74) Attorney, Agent, or Firm — Young Basile Hanlon & MacFarlane, P.C.

(57) ABSTRACT

The present disclosure provides methods of producing cartilage in vitro. The present disclosure provides treatment methods, involving introducing in vitro-produced cartilage into a treatment site in vivo. The present disclosure provides methods of enhancing bone formation, the method involving introducing in vitro-produced hypertrophic cartilage into a treatment site in vivo.

14 Claims, 19 Drawing Sheets

(56) References Cited

OTHER PUBLICATIONS

Nair, et al. Treatment of Goat Femur Segmental Defects with Silica-Coated Hydroxyapatite—One-Year Follow-Up. Tissue Engineering. 16(2): 385-391 (2010).

Narcisi, R., et al. TGF beta-1 administration during ex vivo expansion of human articular chondrocytes in a serum-free medium redirects the cell phenotype toward hypertrophy. Journ. Cell. Physiol. 227(9): 3282-3290 (2012).

Oliviera, et al. Engineering Endochondral Bone: In Vivo Studies. Tissue Engineering, 15(3): 635-643 (2009).

Pelttari, et al. Premature Induction of Hypertrophy During In Vitro Chondrogenesis of Human Mesenchymal Stem Cells Correlates With Calcification and Vascular Invasion After Ectopic Transplantation in SCID Mice. Arthritis Rheum. 54(10):3254-3266 (2006).

Pelttari, et al. The use of mesenchymal stem cells for Chondrogenesis. Injury 3951:S58-S65 (2008).

Safran, et al. The Evidence for Surgical Repair of Articular Cartilage in the Knee. J Am Acad Orthop Surg. 18(5): 259-266 (2010).

Schulez-Tanzi L. Activation and dedifferentiation of chondrocytes: Implications in cartilage injury and repair. Ann Anat. 191(4):325-338 (2009).

Scotti, et al. Recapitulation of endochondral bone formation using human adult mesenchymal stem cells as a paradigm for developmental engineering. Proc. Nati. Acad. Sci. USA. 107:7251 (2010).

Steinert, et al. Hypertrophy is induced during the in vitro chondrogenic differentiation of human mesenchymal stem cells by bone morphogenetic protein-2 and bone morphogenetic protein-4 gene transfer. Arth. Res. Ther. 11:R148 (2009).

Tsukazaki, et al. Parathyroid hormone-related protein (PTHrP) action in rat articular chondrocytes: comparison of PTH(1-34),PTHrP(1-34), PTHrP(1-141) ,PTHrP(100-114)and antisense oligonucleotides against PTHrP. Journal of Endocrinology. 150: 359-368 (1996).

Elisseeff. J., Structure Starts to Gel. Natural Materials, vol. 7, Apr. 2008, pp. 271-273.

Hwang, N, et al., Cartilage Tissue Engineering. Methods of Molecular Biology, vol. 407, Chapter 24; Stem Cell Assays, (ed.) Venuri M.C., Humana Press, Totawa, N.J. pp. 351-373.

Oke, S.L., et al., Development of a Solid-Phase Assay for Measurement of Sulfated Glycosaminoglycan aoncentrations in Equine Synovial Fluid. AJVR, vol. 64, No. 7, Jul. 2003. pp. 894-899.

Patil, A. S., et al., An Update on Transforming Growth Factor-b (TGF-b): Sources, Types, Functions and Clinical Applicability for Cartilage/Bone Healing. Journal of Cellular Physiology, 3094-3103.

Rider, C. C., et al., Bone Morphogenetic Protein and Growth Differentiation Factor Cytokine Families and Their Protein Antagonists. Biochem J. (2010) 429, 1-12.

Rosenberg, L., Chemical Basis for Histological Use of Safranin O in the Study of Articular Cartilage. Journal of Bone and Joint Surgery, vol. 53-A, N. 1, Jan. 1971, pp. 69-82.

Shum, L., et al., BMP4 Promotes Chondrocyte Proliferation and Hypertrophy in the Endochondral Cranial Base. Int. J. Dev. Biol. 47: 423-431 (2003).

Sive, J. I., et al., Expression of Chrondrocyte Markers by Cells of Normal and Degenerate Intervertebral Discs. J Clin Pathol: Mol Pathol 2002; 55: 91-97.

Varghese, S., et al., Chondroitin Sulfate Based Niches for Chondrogenic Differentiation of Mesenchymal Stem Cells, Matrix Biology 27 (2008) 12-21.

Wang, D., et al., Multifunctional Chondroitin Sulphate for Cartilage Tissue-Biomaterial Integration. Nature Materials, vol. 6, May 2007, 385-392.

* cited by examiner

Figure 4
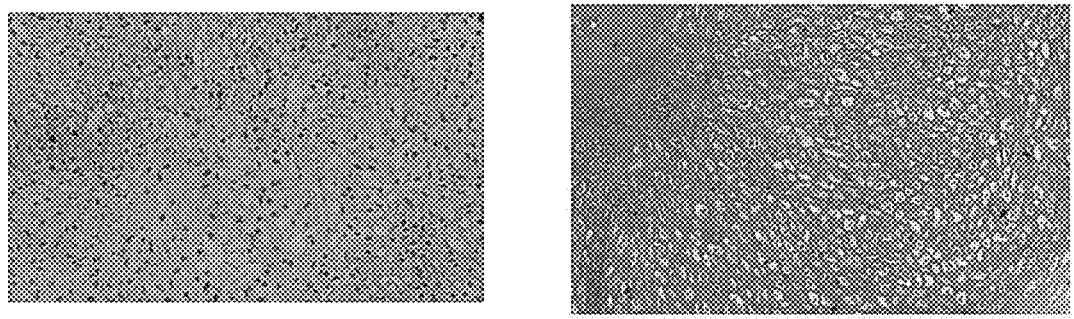
Control chondrocytes
TGF-β1 treatment
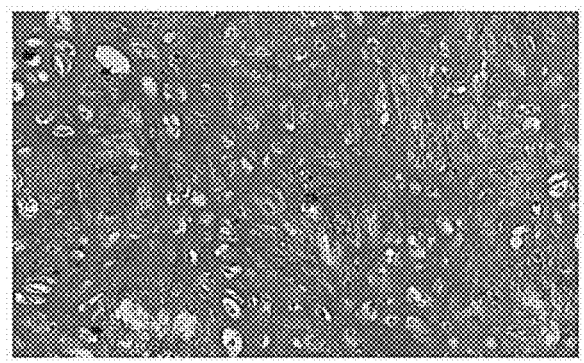
BMP-4 treatment
Figure 5
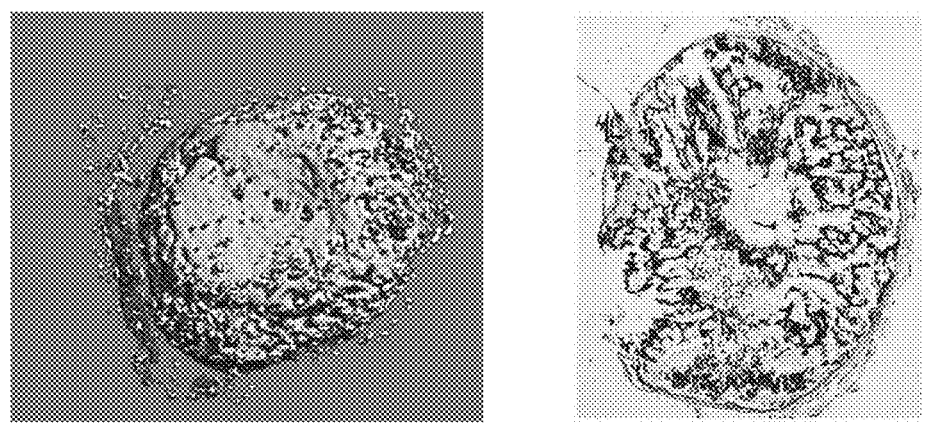

Figure 6

TGF-β1
*Homo sapiens*
GenBank NP_000651.3
Mature peptide = amino acids 279-390

```
  1 mppsgirlip lilpliwllv ltpgrpaagl stcktidmel vkrkrieair gqiilsklrla
 61 sppsqgevpp gplpeavlal ynstrdrvag esaepepepe adyyakevtr vlmvethnei
121 ydkfkqsths iymffntsel reavpepvli sraelrlirl klkveqhvel yqkysnnswr
181 ylsnrllaps dspewlsfdv tgvvrqwlsr ggeiegfrls ahcscdsrdn tlqvdingft
241 tgrrgdlati hgmnrpflli matpleragh lqssrhrral dtnycfsste knccvrqlyi
301 dfrkdlgwkw ihepkgyhan fclgpcpyiw sldtqyskvl alynqhnpga saapccvpqa
361 leplpivyyv grkpkveqls nmivrsckcs
```

TGF-β1
*Mus musculus*
GenBank NP_035707
Mature peptide = amino acids 279-390

```
  1 mppsgirlip lilplpwllv ltpgrpaagl stcktidmel vkrkrieair gqiilsklrla
 61 sppsqgevpp gplpeavlal ynstrdrvag esadpepepe adyyakevtr vlmvdrnnai
121 yektkdishs iymffntsdi reavpeppli sraelrigrl kssveqhvel yqkysnnswr
181 ylgnrlltpt dtpewlsfdv tgvvrqwlnq gdgiqgfrfs ahcscdskdn klhveingis
241 pkrrgdlqti hdmnrpflii matpleragh lhssrhrral dtnycfsste knccvrqlyi
301 dfrkdlgwkw ihepkgyhan fclgpcpyiw sldtqyskvl alynqhnpga saapccvpqa
361 leplpivyyv grkpkveqls nmivrsckcs
```

Figure 7

TGF-β2
*Homo sapiens*
GenBank NP_0032229
Mature peptide = amino acids 303-414

```
  1 mhycvlsafl iihlvtvais lstcstidmd qfmrkrieai rgqilskikl tsppedypep
 61 eevppevisi ynstrdllqe kasrraaace rersdeeyya kevykidmpp ffpsenaipp
121 tfyrpyfriv rfdvsamekn asnlvkaefr vfrlqnpkar vpeqrielyq iikskdltsp
181 tqryidskvv ktraegewls fdvtdavhew lhhkdrnlgf kislhcpcct fvpsnnyiip
241 nkseelearf agidgtstyt sgdqktikst rkknsgktph illmlpsyr lesqqtnrrk
301 kraldaaycf rnvqdncclr plyidfkrdl gwkwihepkg ynanfcagac pylwssdtqh
361 srvislynti npeasaspcc vsqdlepiti lyygktpki eqlsnmivks ckcs
```

TGF-β2
*Mus musculus*
GenBank NP_033393
Mature peptide = amino acids 303-414

```
  1 mhycvlstfl iihlvpvais lstcstidmd qfmrkrieai rgqilskikl tsppedypep
 61 devppevisi ynstrdllqe kasrraaace rersdeeyya kevykidmps hipsenaipp
121 tfyrpyfriv rfdvstmekn asnlvkaefr vfrlqnpkar vaeqrielyq iikskdltsp
181 tqryidskvv ktraegewls fdvtdavgew lhhkdrnlgf kislhcpcct fvpsnnyiip
241 nkseelearf agidgtstya sgdqktikst rkktsgktph illmlpsyr lesqqssrrk
301 kraldaaycf rnvqdncclr plyidfkrdl gwkwihepkg ynanfcagac pylwssdtqh
361 tkvislynti npeasaspcc vsqdlepiti lyyigntpki eqlsnmivks ckcs
```

Figure 8

BMP-4
*Homo sapiens*
GenBank NP_001193
Mature peptide = 293-408

```
  1 mipgnrmlmv vilcqvllgg ashaslipet gkkkvaeiqg haggrrsgqs hellrdfeat
 61 llqmfglrrr pqpsksavip dymrdiyrlq sgeeeeeqih stgleyperp asrantvrsf
121 hheehlenip gtsensairf lfnlssipen evissaeirl freqvdggpd wergihrini
181 iyevmkppae vvpghliitrii dtrlvhhnvt rwetfdvspa vlrwtrekqp nyglaievth
241 lhqtrthgqq hvrisrslpg qsgnwaqlrp llvtfghdgr ghaltrrrra krspkhhsqr
301 arkknkncrr hslyvdfsdv gwndwivapp gyqafychgd cpfpladhin stnhaivqtl
361 vnsvnssipk accvptelsa ismlyldeyd kvvlknygem vvegcgcr
```

BMP-4
*Mus musculus*
GenBank NP_031580
Mature peptide = 293-408

```
  1 mipgnrmlmv vilcqvllgg ashaslipet gkkkvaeiqg haggrrsgqs hellrdfeat
 61 llqmfglrrr pqpsksavip dymrdiyrlq sgeeeeeqs ggtgleyper pasrantvrs
121 fhheehleni pgtsessafrf fifnlsipe nevissaelr lfreqvdggpp dweqgfhrin
181 iyevmkppae mvpghliitri ldtrlvhhnv trwetfdvsp avlrwtrekq pnyglaievt
241 hlhqtrthqq qhvrisrslp qqsgdwaqlr plivtfghdq rghtltrrra krspkhhpqr
301 srkknkncrr hslyvdfsdv gwndwivapp gyqafychgd cpfpladhin stnhaivqtl
361 vnsvnssipk accvptelsa ismlyldeyd kvvlknygem vvegcgcr
```

Figure 9A

Inorganic Salts

| | | | |
|---|---|---|---|
| 5794-13-8 | L-Asparagine Monohydrate | C4H8N2O3.H2O | 7.50000000mg/l |
| 56-86-0 | L-Glutamic Acid | C5H9NO4 | 7.35000000mg/l |
| 657-27-2 | L-Lysine Monohydrochloride | C6H14N2O2.HCL | 91.25000000mg/l |
| 56-45-1 | L-Serine | C3H7NO3 | 26.25000000mg/l |
| 1119-34-2 | L-Arginine Monohydrochloride | C6H14N4O2.HCL | 147.50000000mg/l |
| 72-18-4 | L-Valine | C5H11NO2 | 52.85000000mg/l |
| 30925-07-6 | L-Cystine Dihydrochloride | C6H12N2O4S2.2HCL | 31.29000000mg/l |
| 61-90-5 | L-Leucine | C6H13NO2 | 59.05000000mg/l |
| 147-85-3 | L-Proline | C5H9NO2 | 17.25000000mg/l |
| 56-40-6 | Glycine | C2H5NO2 | 18.75000000mg/l |
| 69847-45-6 | L-Tyrosine Disodium Salt Dihydrate | C9H11NO3+2Na+2H2O | 55.79000000mg/l |
| 7048-04-6 | L-Cysteine Monohydrochloride Monohydrate | C3H7NO2S.HCl.H2O | 17.56000000mg/l |
| 73-32-5 | L-Isoleucine | C6H13NO2 | 54.47000000mg/l |
| 63-91-2 | L-Phenylalanine | C9H11NO2 | 35.48000000mg/l |
| 56-41-7 | L-Alanine | C3H7NO2 | 4.45000000mg/l |
| 73-22-3 | L-Tryptophan | C11H12N2O2 | 9.02000000mg/l |
| 39537-23-0 | L-Alanyl-L-Glutamine | C8H15N3O4 | 365.00000000mg/l |
| 56-84-8 | L-Aspartic acid | C4H7NO4 | 6.65000000mg/l |
| 5934-29-2 | L-Histidine Monohydrochloride Monohydrate | C6H9N3O2.HCL.H2O | 31.48000000mg/l |
| 63-68-3 | L-Methionine | C5H11NO2S | 17.24000000mg/l |
| 72-19-5 | L-Threonine | C4H9NO3 | 53.45000000mg/l |

Vitamins

| | | | |
|---|---|---|---|
| 10035-04-8 | Calcium Chloride Dihydrate | CaCL2.2H2O | 154.50000000mg/l |
| 7791-18-6 | Magnesium Chloride Hexahydrate | MgCL2.6H2O | 61.20000000mg/l |
| 7446-20-0 | Zinc Sulfate Heptahydrate | ZnSO4.7H2O | 0.43200000mg/l |
| 7558-79-4 | Sodium Phosphate Dibasic Anhydrous | Na2HPO4 | 71.02000000mg/l |
| 7782-63-0 | Ferrous Sulfate Heptahydrate | FeO4S.7H2O | 0.41700000mg/l |
| 7647-14-5 | Sodium Chloride | NaCl | 6,996.00000000mg/l |
| 7782-61-8 | Ferric Nitrate Nonahydrate | FeN3O9.9H2O | 0.05000000mg/l |
| 7447-40-7 | Potassium Chloride | KCL | 311.80000000mg/l |
| 7558-80-7 | Sodium Phosphate Monobasic Anhydrous | NaH2PO4 | 54.30000000mg/l |
| 7758-99-8 | Cupric Sulfate Pentahydrate | CuSO4.5H2O | 0.00130000mg/l |
| 7487-88-9 | Magnesium Sulfate Anhydrous | MgSO4 | 48.84000000mg/l |
| 144-55-8 | Sodium Bicarbonate | NaHCO3 | 1,200.00000000mg/l |

Figure 9B

Other Components

| | | | |
|---|---|---|---|
| 98-92-0 | Nicotinamide (Nicotinic acid amide) | C6H6N2O | 2.02000000mg/l |
| 68-19-9 | Vitamine B12 | C63H88CoN14O14P | 0.68000000mg/l |
| 67-48-1 | Choline Chloride | C5H14CLNO | 8.98000000mg/l |
| 87-89-8 | Myo-Inositol | C6H12O6 | 12.60000000mg/l |
| 67-03-8 | Thiamine Hydrochloride | C12H17CLN4OS;HCL | 2.17000000mg/l |
| 65-22-5 | Pyridoxal Hydrochloride | C8H9NO3+HCl | 2.00000000mg/l |
| 59-30-3 | Folic Acid | C19H19N7O6 | 2.66000000mg/l |
| 83-88-5 | Riboflavin | C17H20N4O6 | 0.21900000mg/l |
| 137-08-6 | D-Ca Pantothenate | C18H32CaN2O10 | 2.24000000mg/l |
| 58-56-0 | Pyridoxine Hydrochloride | C8H11NO3;HCL | 0.03100000mg/l |
| 58-85-5 | D-Biotin | C10H16N2O3S | 0.00350000mg/l |
| 34487-61-1 | Phenol Red Sodium Salt | C19 H13 NaO5S | 8.63000000mg/l |
| 60-33-3 | Linoleic acid | C18H32O2 | 0.04200000mg/l |
| 1077-28-7 | Thioctic Acid | C8H14O2S2 | 0.10500000mg/l |
| 68-94-0 | Hypoxanthine | C5H4N4O | 2.10000000mg/l |
| 113-24-6 | Sodium Pyruvate | C3H3O3Na | 55.00000000mg/l |
| 7365-45-9 | Hepes Free Acid | C8H18N2O4S | 3,574.50000000mg/l |
| 333-93-7 | Putrescine+2HCL | C4H12N2 x 2HCl | 0.08100000mg/l |
| 50-89-5 | Thymidine | C10H14N2O5 | 0.36500000mg/l |
| 50-99-7 | D-Glucose Anhydrous | C6H12O6 | 3,151.00000000mg/l |

Figure 10

PTH
*Homo sapiens*
GenBank Accession No. NP_000306
Mature peptide = amino acids 32-115

```
    1 mipakdmakv mivmlaicfl tksdgksvkk rsvseiqlmh nlgkhlnsme
rvewlrkklq
   61 dvhnfvalga plaprdagsq rprkkednvl veshekslge adkadvnvlt kaksq
```

Figure 11

PTHrP
*Homo sapiens*
GenBank Accession No. NP_002811
Mature peptide = amino acids 37-175

```
  1 mqrrlvqqws vavflisyav pscgrsvegl srrikravse hqlihdkgks iqdlrrrffl
 61 hhliaeihta eiratsevsp nskpsnptkn hpvrfgsdde gryitgetnk vetykeqpik
121 tpgkkkkgkp gkrkeqekkk rrtrsawlds gvtgsgiegd hlsdtsttsl eidsr
```

Figure 12

TGF-β3
*Homo sapiens*
GenBank Accession No. NP_003230
Mature peptide = amino acids 301-412

```
  1 mkmhlqraiv vialinfatv sislslstctt dfghikkkrv eairgqilsk lrltsppept
 61 vmthvpyqvl alynstrell eemhgereeg ctqentesey yakeihkfdm iqglaehnel
121 avcpkqitsk vfrfnvssve kqrtnlfrae frvlrvpnps skrneqriel fqilrpdehi
181 akqryiggkn lptrgtaewl sfdvtdtvre wllrresnlg leisihcpch tfqpngdile
241 nihevmeikf kgvdneddhg rgdlgrlkkq kdhhnphlil mmipphrldn pgqgqrkkr
301 aldtnycfrn leenccvrpl yidfrqdlgw kwvhepkgyy anfcsgpcpy lrsadtthst
361 vlglyntinp easaspccvp qdlepltily yvgrtpkveq lsnmvvksck cs
```

Figure 19
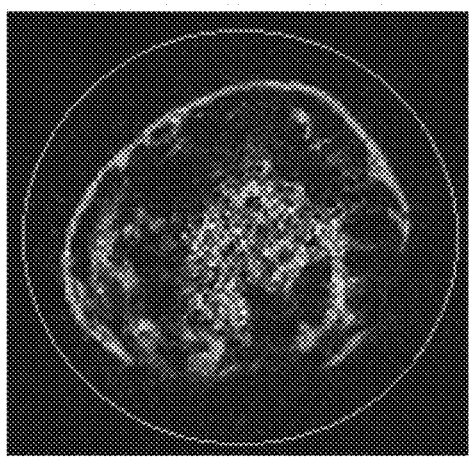 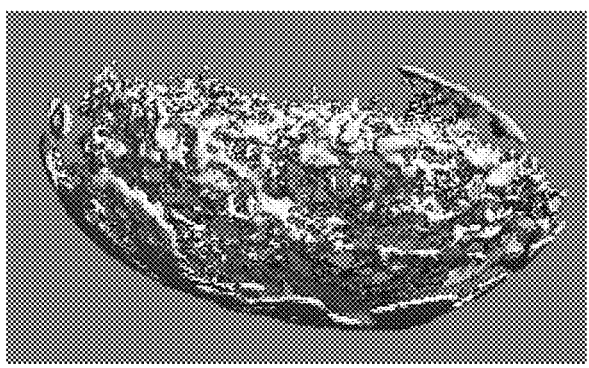

METHODS FOR PRODUCING CARTILAGE AND BONE

CROSS-REFERENCE

This application claims the benefit of U.S. Provisional Patent Application No. 61/673,903 filed Jul. 20, 2012, which application is incorporated herein by reference in its entirety.

INCORPORATION BY REFERENCE OF SEQUENCE LISTING PROVIDED AS A TEXT FILE

A Sequence Listing is provided herewith as a text file, "UCSF-454WO_SeqList_ST25.txt" created on Jul. 15, 2013 and having a size of 29 KB. The contents of the text file are incorporated by reference herein in their entirety.

INTRODUCTION

Articular cartilage injuries are common, lead to pain and disability, and contribute to the development of osteoarthritis. While various cell-based methods are in development for tissue repair, such methods have significant limitations, including lack of an optimal cell source.

Articular chondrocytes and mesenchymal stem cells (MSCs) are commonly used cells for cartilage regeneration. However, articular chondrocytes are available in limited quantities, and MSCs form cartilaginous tissues that do not closely resemble articular cartilage.

There is a need in the art for methods of generating cartilage and bone.

LITERATURE

Fischer et al. (2010) *Arthritis and Rheumatism* 62:2696; Iwata et al. (2012) *Biomaterials* 444:454; Jiang et al. (2010) *Tissue Engineering* 16:1621; Shum et al. (2003) *Int. J. Dev. Biol.* 47:423; Steintert et al. (2009) *Arthr. Res. Ther.* 11:R148; U.S. Pat. No. 6,150,163; U.S. Pat. No. 7,169,610; U.S. Pat. No. 8,017,394; U.S. Patent Publication No. 2003/0175257; Scotti et al. (2010) *Proc. Natl. Acad. Sci. USA* 107:7251; Jukes et al. (2008) *Proc. Natl. Acad. Sci. USA* 105:6840; Gawlitta et al. (2010) *Tissue Engineering* 16:385; Oliviera et al. (2009) *Tissue Engineering* 15:635; U.S. Patent Publication No. 2011/0256109; Brittberg et al. (1994) N Engl J Med. 331(14):889-95; Schulze-Tanzil (2009) Ann Anat. 191(4):325-38; Safran et al. (2010) J Am Acad Orthop Surg. 18(5):259-66; Pelttari et al. (2008) Injury 39 Suppl 1:S58-65; Pelttari et al. (2006) Arthritis Rheum. 54(10):3254-66.

SUMMARY

The present disclosure provides methods of producing cartilage in vitro. The present disclosure provides treatment methods, involving introducing in vitro-produced cartilage into a treatment site in vivo. The present disclosure provides methods of enhancing bone formation, the method involving introducing in vitro-produced hypertrophic cartilage into a treatment site in vivo.

BRIEF DESCRIPTION OF THE DRAWINGS

FIG. 4 depicts passaged chondrocytes cultured in medium including TGF-β1 or BMP-4.

FIG. 5 depicts stimulation of bone formation by hypertrophic cartilage pellets implanted in vivo.

FIG. 6 provides amino acid sequences of TGF-β1 polypeptides. *Homo sapiens* (SEQ ID NO: 1); *Mus musculus* (SEQ ID NO: 2).

FIG. 7 provides amino acid sequences of TGF-β2 polypeptides. *Homo sapiens* (SEQ ID NO: 3); *Mus musculus* (SEQ ID NO: 4).

FIG. 8 provides amino acid sequences of BMP-4 polypeptides. *Homo sapiens* (SEQ ID NO: 5); *Mus musculus* (SEQ ID NO: 6).

FIGS. 9A and 9B provide the composition of an exemplary basal medium.

FIG. 10 provides an amino acid sequence of parathyroid hormone (PTH). (SEQ ID NO: 7).

FIG. 11 provides an amino acid sequence of parathyroid hormone related protein (PTHrP or PTHRP) (SEQ ID NO: 8). An additional isoform is SEQ ID NO: 10.

FIG. 12 provides an aminoa acid sequence of TGF-β3 (SEQ ID NO: 9).

FIG. 19 depicts micro computed tomography (microCT) images of bone formation resulting from implantation of human induced hypertrophic cartilage.

DEFINITIONS

Figure 1:
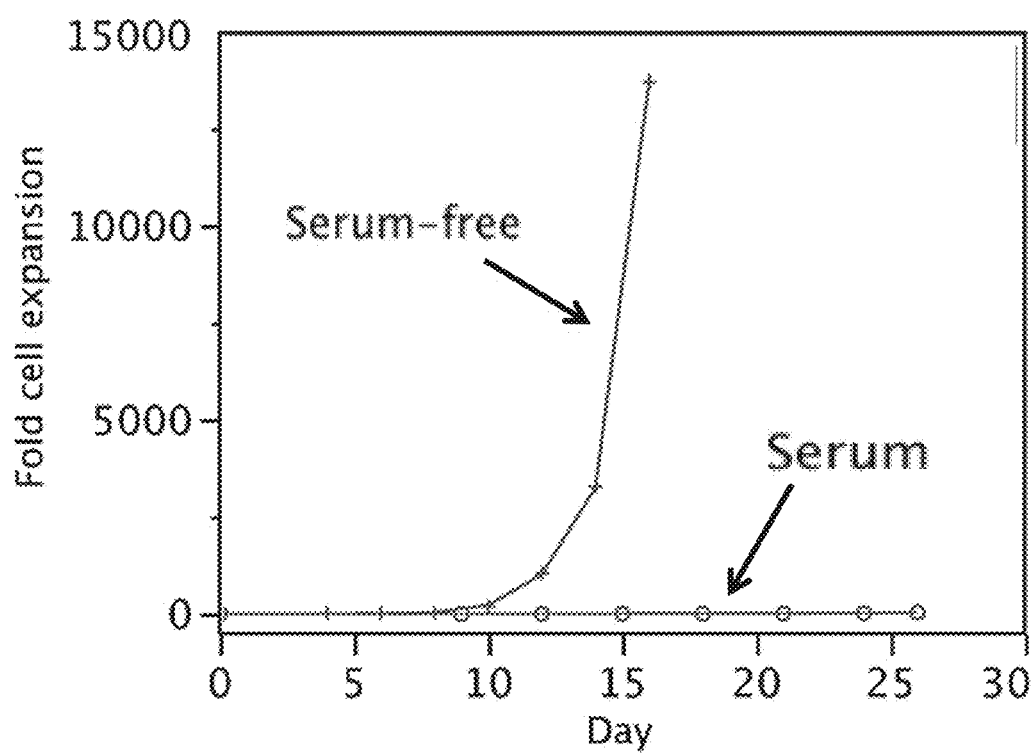
FIG. 1 depicts a comparison of chondrocyte expansion in serum-free medium versus serum-containing medium.

The term "chondrocyte" refers to a cartilage-specific cell that gives rise to normal cartilage tissue growth in vivo; chondrocytes synthesize and deposit the supportive matrix (composed principally of collagen and proteoglycan) of cartilage.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

The terms "treat," "treatment," "treating," and the like are used herein to generally mean obtaining a desired pharmacologic and/or physiologic effect, e.g., increased bone formation. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing the loss of cartilage) from occurring in a subject who may be predisposed to the disease but has not yet been diagnosed as having it; (b) inhibiting the disease, e.g., arresting loss of cartilage; or (c) relieving the disease (e.g., enhancing the development of cartilage).

A "therapeutically effective amount" or "efficacious amount" means the number of cells that, when administered to a mammal or other subject for treating a disease, is sufficient to effect such treatment for the disease, and/or to replace damaged or missing tissue. The "therapeutically effective amount" will vary depending on the cell, the disease and its severity and the age, weight, etc., of the subject to be treated.

As used herein the term "isolated" with reference to a cell, refers to a cell that is in an environment different from that in which the cell naturally occurs, e.g., where the cell naturally occurs in a multicellular organism, and the cell is removed from the multicellular organism, the cell is "isolated."

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chondrocyte" includes a plurality of such chondrocytes and reference to "the composition" includes reference to one or more compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of producing cartilage in vitro. The present disclosure provides treatment methods, involving introducing in vitro-produced cartilage into a treatment site in vivo. The present disclosure provides methods of enhancing bone formation, the method involving introducing in vitro-produced hypertrophic cartilage into a treatment site in vivo.

A method of the present disclosure provides for in vitro amplification of chondrocytes to provide cell numbers sufficient for implantation into a treatment site of an individual. A method of the present disclosure provides for formation, in vitro, of hypertrophic cartilage, which can stimulate the formation of blood vessels when implanted into a treatment site of a mammalian subject. Since bone regeneration requires blood vessel formation, hypertrophic cartilage offers an advantage over bone grafts that do not stimulate formation of blood vessels. Hypertrophic cartilage produced using a subject method can be implanted into a treatment site for tissue repair, and for formation of mineralized bone. A method of the present disclosure can provide for formation, in vitro, of permanent cartilage. Permanent cartilage produced using a subject method can be implanted into a treatment site in an individual, to replace missing cartilage, or to replace diseased or damaged cartilage.

In Vitro Production of Hypertrophic Cartilage

The present disclosure provides methods of producing hypertrophic cartilage in vitro. In carrying out a subject method for producing hypertrophic cartilage, a two-stage procedure is carried out in which chondrocytes are first expanded (first stage), then differentiated (second stage) into hypertrophic cartilage. In some cases, chondrocytes are cultured in a chemically defined, serum-free liquid culture medium in vitro.

The present disclosure thus provides method for producing hypertrophic cartilage in vitro, the method comprising:

a) culturing in a first liquid medium in vitro a starting population of chondrocytes, where the first liquid medium is serum free. Culturing the starting population of chondrocytes provides for an at least 50-fold increase in the number of chondrocytes over the number of chondrocytes in the starting population, thereby generating an expanded chondrocyte population; and b) culturing the expanded chondrocyte in vitro in a second liquid medium, where the second liquid medium is serum free and comprises a transforming growth factor-β (TGFβ) superfamily polypeptide and/or a bone morphogenic protein (BMP). Culturing the expanded chondrocyte population in the second liquid medium results in production of hypertrophic cartilage.

The hypertrophic cartilage thus generated can be directly implanted into a treatment site in an individual. The hypertrophic cartilage thus generated can also be associated with a matrix (scaffold), to generate a hypertrophic cartilage matrix composition; and the hypertrophic cartilage matrix composition can be implanted into a treatment site in an individual.

First Stage

A starting population of chondrocytes is cultured in vitro to expand cell numbers in a first culture medium. This expansion can occur under any conditions. In some cases, the first culture medium is a chemically defined, serum-free liquid culture medium. The first culture medium can include a TGF-β superfamily member (e.g., TGF-β1; TGF-2; TGF-β3; and the like). The starting population of chondrocytes is expanded in the first step (stage), generating an in vitro-expanded population of chondrocytes.

First Culture Medium

The first culture medium includes a basal medium, where any known basal medium suitable for culturing mammalian cells can be used. Suitable basal media include, but are not limited to, Dulbecco's modified Eagle's medium (DMEM), DMEM/F12, Iscove's modified Dulbecco's medium, Minimum Essential Medium, RPMI 1640, and the like. As one non-limiting example, the basal medium is DMEM/F12; the composition of DMEM/F12 is provided in FIGS. 9A and 9B.

The basal medium can be supplemented with, e.g., 50 g/ml ascorbic acid 2-phosphate, 0.1% albumin; 100 μg/ml sodium pyruvate, 100 units/ml penicillin, 100 μg/ml streptomycin, and insulin/transferrin/selenium (ITS; e.g., where the final concentration in the culture medium is 10 mg/L insulin, 5.5 mg/L transferrin, and 6.7 μg/L sodium selenite).

In some cases, the first culture medium is serum-free. In other cases, the first culture medium is not serum-free. In some cases, the first culture medium comprises basal medium supplemented with a TGF-β superfamily protein, such as TGF-β1 (TGFβ1), TGF-β2 (TGFβ32), or TGF-β3 (TGFβ3). TGF-β superfamily proteins are known in the art and are described in, e.g., Patil et al. (2011) *J. Cell. Physiol.* 226:3094. A TGF-β superfamily protein can have a mature peptide length of from about 90 amino acids to about 150 amino acids, e.g., from about 100 amino acids to about 110 amino acids, from about 100 amino acids to about 120 amino acids, etc. In some cases, the first culture medium does not comprise a TGF-β superfamily protein.

TGF-β1 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 120 amino acids of amino acids 279-390 of a TGF-β1 amino acid sequence depicted in FIG. 6 (e.g., set forth in any one of SEQ ID NOs: 1 and 2).

TGF-β2 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 110 amino acids of amino acids 303-414 of a TGF-β2 amino acid sequence depicted in FIG. 7 (e.g., set forth in any one of SEQ ID NOs: 3 and 4).

TGF-β3 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 112 amino acids of amino acids 301-412 of a TGF-β3 amino acid sequence depicted in FIG. 12 (e.g., as set forth in SEQ ID NO: 9).

A TGF-β superfamily protein (e.g., TGF-β1, TGB-β2, TGF-β3, etc.) is present in the first culture medium in a concentration of from about 0.1 ng/ml to about 100 ng/ml, e.g., from about 0.1 ng/ml to about 0.5 ng/ml, from about 0.5 ng/ml to about 1 ng/ml, from about 1 ng/ml to about 5 ng/ml, from about 5 ng/ml to about 10 ng/ml, from about 10 ng/ml to about 25 ng/ml, from about 25 ng/ml to about 50 ng/ml, or from about 50 ng/ml to about 100 ng/ml. In an exemplary embodiment, a TGF-β superfamily protein is present in the culture medium in a concentration of 1 ng/ml.

As one non-limiting example, the first culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; and 1 ng/ml TGF-β1.

In some cases, the chemically-defined, serum-free liquid culture medium does not include one or more of the following components: PDGF; lipids (e.g., stearic acid, myristic acid, oleic acid, linoleic acid, palmitic acid, palmitoleic acid, arachidonic acid, linolenic acid, cholesterol, and alpha-tocopherol acetate); parathyroid hormone-related protein (PTHRP); and parathyroid hormone (PTH). For example, in some cases, the chemically-defined, serum-free liquid culture medium does not include PTHRP. In some cases, the chemically-defined, serum-free liquid culture medium does not include PTHRP or PDGF. In some cases, the chemically-defined, serum-free liquid culture medium does not include PTHRP, PDGF, or a lipid. In some cases, the chemically-defined, serum-free liquid culture medium does not include PTH. In some cases, the chemically-defined, serum-free liquid culture medium does not include PTH, PDGF, or PTHRP.

In the first stage, the starting population of chondrocytes are cultured over a period of time of from about 5 days to about 180 days, e.g., from about 5 days to about 150 days, from about 5 days to about 100 days, from about 5 days to about 75 days, from about 5 days to about 60 days, from about 5 days to about 45 days, from about 5 days to about 30 days, from about 5 days to about 25 days, from about 10 days to about 180 days, from about 10 days to about 150 days, from about 10 days to about 100 days, from about 10 days to about 75 days, from about 10 days to about 60 days, from about 10 days to about 45 days, from about 10 days to about 30 days, from about 10 days to about 25 days, from about 5 days to about 10 days, from about 10 days to about 15 days, from about 15 days to about 20 days, from about 20 days to about 25 days, or from about 25 days to about 30 days.

Cell Numbers

Culturing chondrocytes cultured in vitro as described above results in an increase in the number of chondrocytes, thereby generating an expanded chondrocyte population. For example, culturing a starting population of chondrocytes in a serum-free liquid culture medium, in the presence of a TGFβ superfamily protein and/or a BMP, results in an at least about 50-fold, at least about 75-fold, at least about 100-fold, at least about 250-fold, at least about 500-fold, at least about 1,000-fold, at least about 5,000-fold, at least about 10,000-fold, at least about 15,000-fold, at least about 20,000-fold, or greater than 20,000-fold, increase in the number of chondrocytes relative to the number of chondrocytes in the starting population, where the increase can be over a period of from about 5 days to about 20 days, or from about 10 days to about 15 days, e.g., about 5, 6, 7, 8, 9, 10, 11, 12, 13, 14, 15, 16, 17, 18, 19, or 20 days.

Second Stage

The in vitro expanded chondrocytes generated by the first step are cultured in vitro in a second liquid medium, and includes any process that stimulates hypertrophic differentiation of chondrocytes. In some cases, the second liquid medium is serum free and comprises any molecule that stimulates TGFβ superfamily signaling (a TGFβ polypeptide, e.g., TGFβ1, TGFβ2, TGFβ3; and/or a BMP. Culturing the expanded chondrocyte population in the second liquid medium results in production of hypertrophic cartilage.

During the second stage, the in vitro expanded chondrocytes generated by the first step are cultured in vitro in a second serum-free liquid medium comprising any molecule that stimulates TGFβ superfamily signaling (e.g., a TGFβ polypeptide, e.g., TGFβ1, TGFβ2, TGFβ3; a BMP, e.g., BMP-4; etc.) for a period of time of from about 5 days to about 180 days, e.g., from about 5 days to about 150 days, from about 5 days to about 100 days, from about 5 days to about 75 days, from about 5 days to about 60 days, from about 5 days to about 45 days, from about 5 days to about 30 days, from about 5 days to about 25 days, from about 10 days to about 180 days, from about 10 days to about 150 days, from about 10 days to about 100 days, from about 10 days to about 75 days, from about 10 days to about 60 days, from about 10 days to about 45 days, from about 10 days to about 30 days, from about 10 days to about 25 days, from about 5 days to about 10 days, from about 10 days to about 15 days, from about 15 days to about 20 days, from about 20 days to about 25 days, or from about 25 days to about 30 days.

Second Culture Medium

The second culture medium includes a basal medium, where any known basal medium suitable for culturing mammalian cells can be used. Suitable basal media include, but are not limited to, DMEM, DMEM/F12, Iscove's modified Dulbecco's medium, Minimum Essential Medium, RPMI 1640, and the like. As one non-limiting example, the basal medium is DMEM/F12; the composition of DMEM/F12 is provided in FIGS. 9A and 9B.

The basal medium can be supplemented with, e.g., 50 g/ml ascorbic acid 2-phosphate, 0.1% albumin, 100 µg/ml sodium pyruvate, 100 units/ml penicillin, 100 µg/ml streptomycin, and ITS.

As noted above, the second culture medium can comprise basal medium supplemented with any molecule that stimulates TGFβ superfamily signaling (e.g., a TGFβ polypeptide, e.g., TGFβ1, TGFβ2, TGFβ3; and/or a BMP, e.g., BMP-4).

TGF-β1 suitable for use in the second culture medium can comprise an amino acid sequence having at least about 85%, at least about 90%, at least about 95%, at least about 98%, at least about 99%, or 100%, amino acid sequence identity to a contiguous stretch of from about 100 amino acids to about 120 amino acids of amino acids 279-390 of a TGF-β1 amino acid sequence depicted in FIG. 6 (e.g., set forth in any one of SEQ ID NOs: 1 and 2).

TGF-β2 suitable for use in the second culture medium can comprise an amino acid sequence having at least about 85%, at least about 90%, at least about 95%, at least about 98%, at least about 99%, or 100%, amino acid sequence identity to a contiguous stretch of from about 100 amino acids to about 110 amino acids of amino acids 303-414 of a TGF-β2 amino acid sequence depicted in FIG. 7 (e.g., set forth in any one of SEQ ID NOs: 3 and 4).

TGF-β3 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 112 amino acids of amino acids 301-412 of a TGF-β3 amino acid sequence depicted in FIG. 12 (e.g., as set forth in SEQ ID NO: 9).

A TGF-β superfamily protein (e.g., TGF-β1, TGB-β2, TGF-β3, etc.) is present in the second culture medium in a concentration of from about 0.5 ng/ml to about 100 ng/ml, e.g., from about 0.5 ng/ml to about 1 ng/ml, from about 1 ng/ml to about 5 ng/ml, from about 5 ng/ml to about 10 ng/ml, from about 10 ng/ml to about 25 ng/ml, from about 25 ng/ml to about 50 ng/ml, or from about 50 ng/ml to about 100 ng/ml. In an exemplary embodiment, a TGF-β superfamily protein is present in the second culture medium in a concentration of 10 ng/ml.

A bone morphogenic protein suitable for use can be any BMP that provides the desired effect. A variety of BMP are known in the art. See, e.g., Rider and Mulloy (2010) *Biochem. J.* 429:1. For example, any of the BMP depicted in FIG. 1 of Rider and Mulloy ((2010) *Biochem. J.* 429:1), or an active variant thereof, can be used. For example, a BMP suitable for use can comprise an amino acid sequence having at least about 85%, at least about 90%, at least about 95%, at least about 98%, at least about 99%, or 100%, amino acid sequence identity over a contiguous stretch of at least 100 amino acids to a BMP amino acid sequence depicted in Rider and Mulloy ((2010) *Biochem. J.* 429:1). UniProt accession numbers for the BMP amino acid sequences depicted in Rider and Mulloy ((2010) *Biochem. J.* 429:1) are: BMP-2: P21274; BMP-3: P97737; BMP-4: P21275; BMP-5: P49003; BMP-7: P23359; and BMP-8: P34821. An exemplary BMP-6 amino acid sequence is found under GenBank Accession No. AAB18235. Suitable BMP include, e.g., BMP-1, BMP-2, BMP-3, BMP-4, BMP-5, BMP-6, BMP-7, BMP-8, BMP-9, BMP-10, BMP-11, BMP-12, BMP-13, BMP-14, and BMP-15. In some cases, the BMP included in the second culture medium is BMP-4.

BMP-4 suitable for use in the second culture medium can comprise an amino acid sequence having at least about 85%, at least about 90%, at least about 95%, at least about 98%, at least about 99%, or 100%, amino acid sequence identity to a contiguous stretch of from about 100 amino acids to about 120 amino acids of amino acids 293-408 of a BMP-4 amino acid sequence depicted in FIG. 8 (e.g., set forth in any one of SEQ ID NOs: 5 and 6).

A BMP (e.g., BMP-4) is present in the second culture medium in a concentration of from about 20 ng/ml to about 1000 ng/ml, e.g., from about 20 ng/ml to about 25 ng/ml, from about 25 ng/ml to about 50 ng/ml, from about 50 ng/ml to about 75 ng/ml, from about 75 ng/ml to about 100 ng/ml, from about 100 ng/ml to about 200 ng/ml, from about 200 ng/ml to about 250 ng/ml, from about 250 ng/ml to about 500 ng/ml, from about 500 ng/ml to about 750 ng/ml, or from about 750 ng/ml to about 1000 ng/ml. In an exemplary embodiment, a BMP is present in the second culture medium in a concentration of 200 ng/ml.

In some cases, the chemically-defined, serum-free liquid culture medium does not include one or more of the following components: PDGF; lipids (e.g., stearic acid, myristic acid, oleic acid, linoleic acid, palmitic acid, palmitoleic acid, arachidonic acid, linolenic acid, cholesterol, and alpha-tocopherol acetate); PTHRP; and PTH. For example, in some cases, the chemically-defined, serum-free liquid culture medium does not include PTHRP. In some cases, the chemically-defined, serum-free liquid culture medium does not include PTHRP or PDGF. In some cases, the chemically-defined, serum-free liquid culture medium does not include PTHRP, PDGF, or a lipid. In some cases, the chemically-defined, serum-free liquid culture medium does not include PTH. In some cases, the chemically-defined, serum-free liquid culture medium does not include PTH, PDGF, or PTHRP.

As one non-limiting example, the second culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; and 10 ng/ml TGF-β1.

As a further non-limiting example, the second culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; and 200 ng/ml BMP-4.

As a further non-limiting example, the second culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; 10 ng/ml TGF-β1; and 200 ng/ml BMP-4.

As discussed above, the second culture medium does not include PTHrP. Where the second culture medium does not include PTHrP, hypertrophic cartilage is formed. Hypertrophic cartilage can provide for formation of bone.

Further Culturing

Cells cultured for 5-10 days as described above for the second stage can be further cultured in vitro in serum-free culture medium without a TGB-β superfamily protein and without a BMP. Such further culturing can be carried out over a period of from about 5 days to about 3 months, e.g., from about 5 days to about 10 days, from about 10 days to about 2 weeks, from about 2 weeks to about 4 weeks, or from about 1 month to about 3 months.

The serum-free culture medium can be as described above for the second stage, without a TGB-β superfamily protein and without a BMP. For example, the serum-free culture medium can include DMEM/F12; 0.1% albumin; 50 g/ml ascorbic acid 2-phosphate; 100 μg/ml sodium pyruvate; 100 units/ml penicillin; 100 μg/ml streptomycin; and ITS.

Source of Chondrocytes

Chondrocytes can be obtained from any of a variety of tissue sources. For example, a starting population of chondrocytes can be obtained from hyaline cartilage, elastic cartilage, and fibrocartilage. Chondrocytes can be isolated from bone marrow (e.g., human bone marrow), human bone marrow mesenchymal stromal cells, cartilage (e.g., hyaline cartilage, fibrocartilage, articular cartilage, non-articular cartilage, elastic cartilage, etc.), and the like. Suitable chondrocytes include, but are not limited to, articular chondrocytes (e.g., juvenile articular chondrocytes, adult articular chondrocytes, and the like), nonarticular chondrocytes, synovial capsule chondrocytes, and periosteum chondrocytes.

Chondrocytes can be obtained from any age, species, and health. For example, chondrocytes can be obtained from any of a variety of mammals, including, but not limited to, humans, non-human primates, porcines, murines (e.g., mice), bovine, and the like. In some cases, the source of the chondrocytes will be the same species as the prospective recipient of hypertrophic cartilage generated from the chondrocytes. For example, in some embodiments, chondrocytes will be obtained from a human; the chondrocytes will be cultured in vitro to generate hypertrophic cartilage; and the hypertrophic cartilage thus generated will be implanted into a treatment site in a human. In other cases, the source of the chondrocyte will be a different species from the prospective recipient of hypertrophic cartilage.

In some instances, the individual from whom chondrocytes are obtained is the same as the prospective recipient of hypertrophic cartilage generated from the chondrocytes; i.e., the chondrocytes will be autologous to the prospective recipient. In other instances, the individual from whom chondrocytes are obtained is the same species, but different from the prospective recipient of hypertrophic cartilage generated from the chondrocytes; i.e., the chondrocytes will be allogeneic to the prospective recipient.

Thus, relative to an intended recipient of a subject cell composition, hypertrophic cartilage-producing chondrocytes can be autologous, allogeneic, or xenogeneic. For example, where the intended or prospective recipient of a subject hypertrophic cartilage composition is a human, the cells present in the hypertrophic cartilage composition can be human cells. Where the intended or prospective recipient of a subject hypertrophic cartilage composition is a human, the cells present in a subject hypertrophic cartilage composition can be autologous or allogeneic. Where the intended or prospective recipient of a subject hypertrophic cartilage composition is a human, the cells present in a subject hypertrophic cartilage composition can in some cases be xenogeneic.

Chondrocytes can be obtained from tissue of any age and/or health, including, but not limited to fetal tissue, neonatal tissue, post-natal tissue, juvenile tissue, and adult tissue, etc (e.g., chondrocytes can be articular chondrocytes from an osteoarthritic human joint, also known as human osteoarthritic articular chondrocytes).

Chondrocytes can be isolated from a tissue source using any well-known method. As one non-limiting example, articular cartilage can be harvested from femoral condyles of human donors, and chondrocytes can be released from the cartilage by overnight digestion in 0.1% collagenase.

Purity

Generally, chondrocytes that are cultured in vitro according to a method of the present disclosure are isolated, e.g., purified. For example, chondrocytes present in a population of chondrocytes are at least about 85%, at least about 90%, at least about 95%, at least about 98%, at least about 99%, or greater than 99% (e.g., 99.5%, 99.8%, 99.9%, etc.), pure, where "pure" indicates that a population of chondrocytes is substantially free of cells other than chondrocytes. For example, a "pure" population of chondrocytes is a population of chondrocytes that is substantially free of mesenchymal stem cells (MSCs). For example, the starting population of chondrocytes is pure; and the expanded population of chondrocytes is pure.

Gene Expression

Chondrocytes cultured in vitro as described above express one or more of the following (as mRNA and/or protein):

aggrecan (ACAN); type II collagen (Col2); Sox9. See, e.g., Sive et al. ((2002) *Mol. Pathol.* 55:91) for a discussion of chondrocyte markers.

Chondrocytes express one or more of the following markers: 11-fibrau; aggrecan; annexin VI; beta-1 integrin (CD29); cartilage oligomeric matrix protein (COMP); cathepsin B; CD44, CD151, and CD49c; chondrocyte expressed protein-68 (CEP-68); cartilage matrix protein (CMP; matrilin-1); collagen II (type II collagen); collagen IX; Sox9; and collagen X (type X collagen). Chondrocytes can be identified as, e.g., $CD29^+$, $CD90^+$, $CD166^+$, $CD49^+$, $CD44^+$, $CD54^+$, $CD14^-$, $CD34^-$, $CD24^-$, and $CD31^-$.

Chondrocytes can be characterized by secretion of one or more of the following: type II collagen; type X collagen; and a proteoglycan such as aggrecan. Aggrecan is a proteoglycan comprising a protein core that is modified with glycosaminoglycans (GAG) such as chondroitin sulfate and keratan sulfate. Whether a chondrocyte secretes aggrecan can be determined by detecting the presence of GAG. GAG can be detected using any known assay, including, e.g., a 1,9-dimethylmethylene blue (DMMB) assay (see, e.g., Oke et al. (2003) *Am. J. Vet. Res.* 64:894); and a safranin-O staining method (see, e.g., Rosenberg (1971) *J. Bone Joint Surg.* 53:69)

In some cases, a subject in vitro culture method increases Col2 gene expression, relative to beta-2 microglobulin ($\beta 2M$) by at least about 25%, at least about 50%, at least about 2-fold, at least about 2.5-fold, at least about 3-fold, at least about 4-fold, at least about 5-fold, at least about 10-fold, or more than 10-fold, compared with Col2 gene expression in chondrocytes cultured in serum-free culture medium in the absence of a TGF$\beta$ superfamily protein and/or a BMP.

In some cases, a subject in vitro culture method increases ACAN gene expression, relative to $\beta 2M$ by at least about 25%, at least about 50%, at least about 2-fold, at least about 2.5-fold, at least about 3-fold, at least about 4-fold, at least about 5-fold, at least about 10-fold, or more than 10-fold, compared with ACAN gene expression in chondrocytes cultured in serum-free culture medium in the absence of a TGF$\beta$ superfamily protein and/or a BMP.

Gene expression can be determined using any of a variety of well-known methods, which include, e.g., quantitative polymerase chain reaction (qPCR) to determine the level of an mRNA product in a cell. Such methods can entail the use of nucleic acid primer pairs that specifically amplify a particular mRNA (or a cDNA copy of a particular mRNA), such as an aggrecan mRNA, a type 2 collagen mRNA, a Sox9 mRNA, and the like. Gene expression can also be determined by detecting a polypeptide product, using any of a variety of well-known methods, such as immunological methods, including, e.g., enzyme-linked immunosorbent assay (ELISA), immunoprecipitation assay, a Western blot assay, and the like. Antibody specific for the polypeptide product (e.g., aggrecan, collagen type 2, etc.) can be used.

Morphology

Chondrocytes cultured in vitro as described above assume a hypertrophic morphology. Chondrocytes cultured in vitro as described above resemble native articular cartilage, e.g., when cultured over a period of from about 5 days to about 20 days, or from about 10 days to about 15 days.

In Vitro Production of Permanent Cartilage

The present disclosure provides methods of producing permanent cartilage in vitro. In carrying out a subject method for producing permanent cartilage, a two-stage procedure is carried out in which chondrocytes are first expanded (first stage), then differentiated (second stage) into permanent cartilage. In some cases, chondrocytes are cultured in a chemically defined, serum-free liquid culture medium in vitro. In these methods, in some cases, the second culture medium includes PTHrP and/or PTH in addition to any molecule that stimulates TGF$\beta$ superfamily signaling (a TGF$\beta$ polypeptide, e.g., TGF$\beta$1, TGF$\beta$2, TGF$\beta$3; and/or a BMP, e.g., BMP-4). Permanent cartilage does not provide for formation of bone. Permanent cartilages include articular cartilage. Thus, inclusion of PTHrP in the second culture medium (in addition to a TGF-$\beta$ superfamily protein and/or a BMP), leads to formation of permanent cartilage.

Permanent cartilage includes articular cartilage, fibrocartilage, and elastic cartilage. Articular cartilage covers the articulating surfaces of the portions of bones in joints. Intraarticular fibrocartilages are found in those joints which are most exposed to violent concussion and subject to frequent movement, e.g., the meniscus of the knee. Examples of such joints include the temporo-mandibular, sterno-clavicular, acromio-clavicular joints. Elastic cartilage contains collagen fibers that are histologically similar to elastin fibers. Such cartilage is found in the human body in the auricle of the external ear, the Eustachian tubes, the cornicula laryngis, and the epiglottis.

Thus, in some embodiments, the present disclosure provides a method of generating permanent cartilage, the method comprising:
  a) culturing in a first liquid medium in vitro a starting population of chondrocytes, where the first liquid medium is serum free. Culturing the starting population of chondrocytes provides for an at least 50-fold increase in the number of chondrocytes over the number of chondrocytes in the starting population, thereby generating an expanded chondrocyte population; and
  b) culturing the expanded chondrocyte in vitro in a second liquid medium, where the second liquid medium is serum free and comprises any molecule that stimulates TGF$\beta$ superfamily signaling (a TGF$\beta$ polypeptide, e.g., TGF$\beta$1, TGF$\beta$2, TGF$\beta$3; and/or a BMP, e.g., BMP-4), and further comprises PTHrP. Culturing the expanded chondrocyte population in the second liquid medium results in production of permanent cartilage.

The first stage, the first stage culture medium, the TGF-$\beta$ superfamily protein, and the BMP are as described for in vitro production of hypertrophic cartilage.

First Stage

A starting population of chondrocytes is cultured in vitro to expand cell numbers in a first culture medium. This expansion can occur under any conditions. In some cases, the first culture medium is a chemically defined, serum-free liquid culture medium. The first culture medium can include a TGF-$\beta$ superfamily member (e.g., TGF-$\beta$1; TGF-2; TGF-$\beta$3; and the like). The starting population of chondrocytes is expanded in the first step (stage), generating an in vitro-expanded population of chondrocytes.

First Culture Medium

The first culture medium includes a basal medium, where any known basal medium suitable for culturing mammalian cells can be used. Suitable basal media include, but are not limited to, DMEM, DMEM/F12, Iscove's modified Dulbecco's medium, Minimum Essential Medium, RPMI 1640, and the like. As one non-limiting example, the basal medium is DMEM/F12; the composition of DMEM/F12 is provided in FIGS. 9A and 9B.

The basal medium can be supplemented with, e.g., 50 g/ml ascorbic acid 2-phosphate, 0.1% albumin, 100 µg/ml sodium pyruvate, 100 units/ml penicillin, 100 µg/ml streptomycin, and insulin/transferrin/selenium (ITS; e.g., where the final concentration in the culture medium is 10 mg/L insulin, 5.5 mg/L transferrin, and 6.7 µg/L sodium selenite).

In some cases, the first culture medium is serum-free. In other cases, the first culture medium is not serum-free. In some cases, the first culture medium comprises basal medium supplemented with a TGF-β superfamily protein, such as TGF-β1 (TGFβ1), TGF-β2 (TGFβ32), or TGF-β3 (TGFβ3). In some cases, the first culture medium does not comprise a TGF-β superfamily protein.

TGF-β1 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 120 amino acids of amino acids 279-390 of a TGF-β1 amino acid sequence depicted in FIG. 6 (e.g., set forth in any one of SEQ ID NOs: 1 and 2).

TGF-β2 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 110 amino acids of amino acids 303-414 of a TGF-β2 amino acid sequence depicted in FIG. 7 (e.g., set forth in any one of SEQ ID NOs: 3 and 4).

TGF-β3 suitable for use in the first culture medium can comprise an amino acid sequence having at least about 85%, at least about 90%, at least about 95%, at least about 98%, at least about 99%, or 100%, amino acid sequence identity to a contiguous stretch of from about 100 amino acids to about 112 amino acids of amino acids 301-412 of a TGF-β3 amino acid sequence depicted in FIG. 12 (e.g., as set forth in SEQ ID NO: 9).

A TGF-β superfamily protein (e.g., TGF-β1, TGB-β2, etc.) is present in the first culture medium in a concentration of from about 0.1 ng/ml to about 100 ng/ml, e.g., from about 0.1 ng/ml to about 0.5 ng/ml, from about 0.5 ng/ml to about 1 ng/ml, from about 1 ng/ml to about 5 ng/ml, from about 5 ng/ml to about 10 ng/ml, from about 10 ng/ml to about 25 ng/ml, from about 25 ng/ml to about 50 ng/ml, or from about 50 ng/ml to about 100 ng/ml. In an exemplary embodiment, a TGF-β superfamily protein is present in the culture medium in a concentration of 1 ng/ml.

As one non-limiting example, the first culture medium includes DMEM/F12; 50 g/ml ascorbic acid 2-phosphate; 0.1% albumin; 100 µg/ml sodium pyruvate; 100 units/ml penicillin; 100 µg/ml streptomycin; ITS; and 1 ng/ml TGF-β1.

In some cases, the chemically-defined, serum-free liquid culture medium does not include one or more of the following components: PDGF; lipids (e.g., stearic acid, myristic acid, oleic acid, linoleic acid, palmitic acid, palmitoleic acid, arachidonic acid, linolenic acid, cholesterol, and alpha-tocopherol acetate); parathyroid hormone-related protein (PTHrP); and parathyroid hormone (PTH). For example, in some cases, the chemically-defined, serum-free liquid culture medium does not include PTHrP. In some cases, the chemically-defined, serum-free liquid culture medium does not include PTHrP or PDGF. In some cases, the chemically-defined, serum-free liquid culture medium does not include PTHRP, PDGF, or a lipid. In some cases, the chemically-defined, serum-free liquid culture medium does not include PTH. In some cases, the chemically-defined, serum-free liquid culture medium does not include PTH, PDGF, or PTHRP.

In the first stage, the starting population of chondrocytes are cultured over a period of time of from about 5 days to about 180 days, e.g., from about 5 days to about 150 days, from about 5 days to about 100 days, from about 5 days to about 75 days, from about 5 days to about 60 days, from about 5 days to about 45 days, from about 5 days to about 30 days, from about 5 days to about 25 days, from about 10 days to about 180 days, from about 10 days to about 150 days, from about 10 days to about 100 days, from about 10 days to about 75 days, from about 10 days to about 60 days, from about 10 days to about 45 days, from about 10 days to about 30 days, from about 10 days to about 25 days, from about 5 days to about 10 days, from about 10 days to about 15 days, from about 15 days to about 20 days, from about 20 days to about 25 days, or from about 25 days to about 30 days.

Cell Numbers

Culturing chondrocytes cultured in vitro as described above results in an increase in the number of chondrocytes, thereby generating an expanded chondrocyte population. For example, culturing a starting population of chondrocytes in a serum-free liquid culture medium, in the presence of any molecule that stimulates TGFβ superfamily signaling (a TGFβ polypeptide, e.g., TGFβ1, TGFβ2, TGFβ3; and/or a BMP, e.g., BMP-4), results in an at least about 50-fold, at least about 75-fold, at least about 100-fold, at least about 250-fold, at least about 500-fold, at least about 1,000-fold, at least about 5,000-fold, at least about 10,000-fold, at least about 15,000-fold, at least about 20,000-fold, or greater than 20,000-fold, increase in the number of chondrocytes relative to the number of chondrocytes in the starting population, where the increase can be over a period of from about 5 days to about 20 days, or from about 10 days to about 15 days, e.g., about 5, 6, 7, 8, 9, 10, 11, 12, 13, 14, 15, 16, 17, 18, 19, or 20 days.

Second Stage

The in vitro expanded chondrocytes generated by the first step are cultured in vitro in a second liquid medium, and includes any process that stimulates hypertrophic differentiation of chondrocytes. In some cases, the second liquid medium is serum free and comprises any molecule that stimulates TGFβ superfamily signaling (a TGFβ polypeptide, e.g., TGFβ1, TGFβ2, TGFβ3; and/or a BMP, e.g., BMP-4), and can further comprise PTHrP and/or PTH. Culturing the expanded chondrocyte population in the second liquid medium results in production of permanent cartilage.

During the second stage, the in vitro expanded chondrocytes generated by the first step are cultured in vitro in a second serum-free liquid medium comprising any molecule that stimulates TGFβ superfamily signaling (e.g., a TGFβ polypeptide, e.g., TGFβ1, TGFβ2, TGFβ3; and/or a BMP, e.g., BMP-4; etc) for a period of time of from about 5 days to about 180 days, e.g., from about 5 days to about 150 days, from about 5 days to about 100 days, from about 5 days to about 75 days, from about 5 days to about 60 days, from about 5 days to about 45 days, from about 5 days to about 30 days, from about 5 days to about 25 days, from about 10 days to about 180 days, from about 10 days to about 150 days, from about 10 days to about 100 days, from about 10 days to about 75 days, from about 10 days to about 60 days, from about 10 days to about 45 days, from about 10 days to about 30 days, from about 10 days to about 25 days, from about 5 days to about 10 days, from about 10 days to about 15 days, from about 15 days to about 20 days, from about 20 days to about 25 days, or from about 25 days to about 30 days.

Second Culture Medium

The second culture medium includes a basal medium, where any known basal medium suitable for culturing mammalian cells can be used. Suitable basal media include, but are not limited to, DMEM, DMEM/F12, Iscove's modified Dulbecco's medium, Minimum Essential Medium, RPMI 1640, and the like. As one non-limiting example, the basal medium is DMEM/F12; the composition of DMEM/F12 is provided in FIGS. 9A and 9B.

The basal medium can be supplemented with, e.g., 50 g/ml ascorbic acid 2-phosphate, 0.1% albumin, 100 μg/ml sodium pyruvate, 100 units/ml penicillin, 100 μg/ml streptomycin, and ITS.

In some cases, the chemically-defined, serum-free liquid culture medium does not include one or more of the following components: PDGF; lipids (e.g., stearic acid, myristic acid, oleic acid, linoleic acid, palmitic acid, palmitoleic acid, arachidonic acid, linolenic acid, cholesterol, and alpha-tocopherol acetate). In some cases, the chemically-defined, serum-free liquid culture medium does not include PDGF. In some cases, the chemically-defined, serum-free liquid culture medium does not include PDGF, or a lipid. In some cases, the chemically-defined, serum-free liquid culture medium does not include PTH.

As noted above, the second culture medium can comprise basal medium supplemented with any molecule that stimulates TGFβ superfamily signaling (e.g., a TGFβ polypeptide, e.g., TGFβ1, TGFβ2, TGFβ3; and/or a BMP, e.g., BMP-4); and further includes PTHrP.

TGF-β1 suitable for use in the second culture medium can comprise an amino acid sequence having at least about 85%, at least about 90%, at least about 95%, at least about 98%, at least about 99%, or 100%, amino acid sequence identity to a contiguous stretch of from about 100 amino acids to about 120 amino acids of amino acids 279-390 of a TGF-β1 amino acid sequence depicted in FIG. 6 (e.g., set forth in any one of SEQ ID NOs: 1 and 2).

TGF-β2 suitable for use in the second culture medium can comprise an amino acid sequence having at least about 85%, at least about 90%, at least about 95%, at least about 98%, at least about 99%, or 100%, amino acid sequence identity to a contiguous stretch of from about 100 amino acids to about 110 amino acids of amino acids 303-414 of a TGF-β2 amino acid sequence depicted in FIG. 7 (e.g., set forth in any one of SEQ ID NOs: 3 and 4).

A TGF-β superfamily protein (e.g., TGF-β1, TGB-β2, etc.) is present in the second culture medium in a concentration of from about 0.5 ng/ml to about 100 ng/ml, e.g., from about 0.5 ng/ml to about 1 ng/ml, from about 1 ng/ml to about 5 ng/ml, from about 5 ng/ml to about 10 ng/ml, from about 10 ng/ml to about 25 ng/ml, from about 25 ng/ml to about 50 ng/ml, or from about 50 ng/ml to about 100 ng/ml. In an exemplary embodiment, a TGF-β superfamily protein is present in the second culture medium in a concentration of 10 ng/ml.

A bone morphogenic protein suitable for use can be any BMP that provides the desired effect. A variety of BMP are known in the art. See, e.g., Rider and Mulloy (2010) *Biochem. J.* 429:1. For example, any of the BMP depicted in FIG. 1 of Rider and Mulloy ((2010) *Biochem. J.* 429:1), or an active variant thereof, can be used. For example, a BMP suitable for use can comprise an amino acid sequence having at least about 85%, at least about 90%, at least about 95%, at least about 98%, at least about 99%, or 100%, amino acid sequence identity over a contiguous stretch of at least 100 amino acids to a BMP amino acid sequence depicted in Rider and Mulloy ((2010) *Biochem. J.* 429:1). UniProt accession numbers for the BMP amino acid sequences depicted in Rider and Mulloy ((2010) *Biochem. J.* 429:1) are: BMP-2: P21274; BMP-3: P97737; BMP-4: P21275; BMP-5: P49003; BMP-7: P23359; and BMP-8: P34821. An exemplary BMP-6 amino acid sequence is found under GenBank Accession No. AAB18235. Suitable BMP include, e.g., BMP-1, BMP-2, BMP-3, BMP-4, BMP-5, BMP-6, BMP-7, BMP-8, BMP-9, BMP-10, BMP-11, BMP-12, BMP-13, BMP-14, and BMP-15. In some cases, the BMP included in the second culture medium is BMP-4.

BMP-4 suitable for use in the second culture medium can comprise an amino acid sequence having at least about 85%, at least about 90%, at least about 95%, at least about 98%, at least about 99%, or 100%, amino acid sequence identity to a contiguous stretch of from about 100 amino acids to about 120 amino acids of amino acids 293-408 of a BMP-4 amino acid sequence depicted in FIG. 8 (e.g., set forth in any one of SEQ ID NOs: 5 and 6).

A BMP (e.g., BMP-4) is present in the second culture medium in a concentration of from about 20 ng/ml to about 1000 ng/ml, e.g., from about 20 ng/ml to about 25 ng/ml, from about 25 ng/ml to about 50 ng/ml, from about 50 ng/ml to about 75 ng/ml, from about 75 ng/ml to about 100 ng/ml, from about 100 ng/ml to about 200 ng/ml, from about 200 ng/ml to about 250 ng/ml, from about 250 ng/ml to about 500 ng/ml, from about 500 ng/ml to about 750 ng/ml, or from about 750 ng/ml to about 1000 ng/ml. In an exemplary embodiment, a BMP is present in the second culture medium in a concentration of 200 ng/ml.

PTHrP suitable for use in the second culture medium can comprise an amino acid sequence having at least about 85%, at least about 90%, at least about 95%, at least about 98%, at least about 99%, or 100%, amino acid sequence identity to a contiguous stretch of from about 50 amino acids to about 139 amino acids of amino acids 37-175 of a PTHrP amino acid sequence depicted in FIG. 11 (e.g., set forth in any of SEQ ID NOs: 8 and 10) (SEQ ID NO: 10 is an isoform of SEQ NO: 8).

PTHrP can be present in the second culture medium in a concentration range of from about 10 nM to about 1000 nM, e.g., from about 10 nM to about 50 nM, from about 50 nM to about 100 nM, from about 100 nM to about 250 nM, from about 250 nM to about 500 nM, from about 500 nM to about 750 nM, or from about 750 nM to about 1000 nM. In some cases, PTHrP is present in the second culture medium in a concentration of 100 nM.

As one non-limiting example, the second culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; 10 ng/ml TGF-β1; and 100 nM PTHrP.

As a further non-limiting example, the second culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; 200 ng/ml BMP-4; and 100 nM PTHrP.

As a further non-limiting example, the second culture medium includes DMEM/F12; 50 g/ml ascorbic acid 2-phosphate; 0.1% albumin; 100 μg/ml sodium pyruvate; 100 units/ml penicillin; 100 μg/ml streptomycin; ITS; 10 ng/ml TGF-β1; 200 ng/ml BMP-4; and 100 nM PTHrP.

In some cases, PTH is used instead of PTHrP. PTH suitable for use in the second culture medium can comprise an amino acid sequence having at least about 85%, at least about 90%, at least about 95%, at least about 98%, at least about 99%, or 100%, amino acid sequence identity to a contiguous stretch of from about 50 amino acids to about 84 amino acids of amino acids 32-115 of a PTH amino acid sequence depicted in FIG. 10 (e.g., as set forth in SEQ ID NO: 7).

Further Culturing

Cells cultured for 5-10 days as described above for the second stage can be further cultured in vitro in serum-free culture medium without a TGB-β superfamily protein, without a BMP, and without PTHrP. Such further culturing can be carried out over a period of from about 5 days to about 3 months, e.g., from about 5 days to about 10 days, from about 10 days to about 2 weeks, from about 2 weeks to about 4 weeks, or from about 1 month to about 3 months.

The serum-free culture medium can be as described above for the second stage, without a TGB-β superfamily protein, without a BMP, and without PTHrP. For example, the serum-free culture medium can include DMEM/F12; 0.1% albumin; 50 g/ml ascorbic acid 2-phosphate; 100 µg/ml sodium pyruvate; 100 units/ml penicillin; 100 µg/ml streptomycin; and ITS.

Source of Chondrocytes

Chondrocytes can be obtained from any of a variety of tissue sources. For example, a starting population of chondrocytes can be obtained from hyaline cartilage, elastic cartilage, and fibrocartilage. Chondrocytes can be isolated from bone marrow (e.g., human bone marrow), human bone marrow mesenchymal stromal cells, cartilage (e.g., hyaline cartilage, fibrocartilage, articular cartilage, non-articular cartilage, elastic cartilage, etc.), and the like. Suitable chondrocytes include, but are not limited to, articular chondrocytes (e.g., juvenile articular chondrocytes, adult articular chondrocytes, and the like), nonarticular chondrocytes, synovial capsule chondrocytes, and periosteum chondrocytes.

Chondrocytes can be obtained from any age, species, and health. For example, chondrocytes can be obtained from any of a variety of mammals, including, but not limited to, humans, non-human primates, porcines, murines (e.g., mice), bovine, and the like. In some cases, the source of the chondrocytes will be the same species as the prospective recipient of hypertrophic cartilage generated from the chondrocytes. For example, in some embodiments, chondrocytes will be obtained from a human; the chondrocytes will be cultured in vitro to generate hypertrophic cartilage; and the hypertrophic cartilage thus generated will be implanted into a treatment site in a human. In other cases, the source of the chondrocyte will be a different species from the prospective recipient of hypertrophic cartilage.

In some instances, the individual from whom chondrocytes are obtained is the same as the prospective recipient of permanent cartilage generated from the chondrocytes; i.e., the chondrocytes will be autologous to the prospective recipient. In other instances, the individual from whom chondrocytes are obtained is the same species, but different from the prospective recipient of permanent cartilage generated from the chondrocytes; i.e., the chondrocytes will be allogeneic to the prospective recipient.

Thus, relative to an intended recipient of a subject cell composition, permanent cartilage-producing chondrocytes can be autologous, allogeneic, or xenogeneic. For example, where the intended or prospective recipient of a subject permanent cartilage composition is a human, the cells present in the hypertrophic cartilage composition can be human cells. Where the intended or prospective recipient of a subject permanent cartilage composition is a human, the cells present in a subject permanent cartilage composition can be autologous or allogeneic. Where the intended or prospective recipient of a subject permanent cartilage composition is a human, the cells present in a subject hypertrophic cartilage composition can in some cases be xenogeneic.

Chondrocytes can be obtained from tissue of any age and/or health, including, but not limited to fetal tissue, neonatal tissue, post-natal tissue, juvenile tissue, and adult tissue, etc (e.g., chondrocytes can be articular chondrocytes from an osteoarthritic human joint, also known as human osteoarthritic articular chondrocytes).

Chondrocytes can be isolated from a tissue source using any well-known method. As one non-limiting example, articular cartilage can be harvested from femoral condyles of human donors, and chondrocytes can be released from the cartilage by overnight digestion in 0.1% collagenase.

Purity

Generally, chondrocytes that are cultured in vitro according to a method of the present disclosure are isolated, e.g., purified. For example, chondrocytes present in a population of chondrocytes are at least about 85%, at least about 90%, at least about 95%, at least about 98%, at least about 99%, or greater than 99% (e.g., 99.5%, 99.8%, 99.9%, etc.), pure, where "pure" indicates that a population of chondrocytes is substantially free of cells other than chondrocytes. For example, a "pure" population of chondrocytes is a population of chondrocytes that is substantially free of mesenchymal stem cells (MSCs). For example, the starting population of chondrocytes is pure; and the expanded population of chondrocytes is pure.

Gene Expression

Chondrocytes cultured in vitro as described above express one or more of the following (as mRNA and/or protein): aggrecan (ACAN); type II collagen (Col2); Sox9. See, e.g., Sive et al. ((2002) *Mol. Pathol.* 55:91) for a discussion of chondrocyte markers.

Chondrocytes express one or more of the following markers: 11-fibrau; aggrecan; annexin VI; beta-1 integrin (CD29); cartilage oligomeric matrix protein (COMP); cathepsin B; CD44, CD151, and CD49c; chondrocyte expressed protein-68 (CEP-68); cartilage matrix protein (CMP; matrilin-1); collagen II (type II collagen); collagen IX; Sox9; and collagen X (type X collagen). Chondrocytes can be identified as, e.g., $CD29^+$, $CD90^+$, $CD166^+$, $CD49^+$, $CD44^+$, $CD54^+$, $CD14^-$, $CD34^-$, $CD24^-$, and $CD31^-$.

Chondrocytes can be characterized by secretion of one or more of the following: type II collagen; type X collagen; and a proteoglycan such as aggrecan. Aggrecan is a proteoglycan comprising a protein core that is modified with glycosaminoglycans (GAG) such as chondroitin sulfate and keratan sulfate. Whether a chondrocyte secretes aggrecan can be determined by detecting the presence of GAG. GAG can be detected using any known assay, including, e.g., a 1,9-dimethylmethylene blue (DMMB) assay (see, e.g., Oke et al. (2003) *Am. J. Vet. Res.* 64:894); and a safranin-O staining method (see, e.g., Rosenberg (1971) *J. Bone Joint Surg.* 53:69)

In some cases, a subject in vitro culture method increases Col2 gene expression, relative to beta-2 microglobulin (β2M) by at least about 25%, at least about 50%, at least about 2-fold, at least about 2.5-fold, at least about 3-fold, at least about 4-fold, at least about 5-fold, at least about 10-fold, or more than 10-fold, compared with Col2 gene expression in chondrocytes cultured in serum-free culture medium in the absence of a TGFβ superfamily protein and/or a BMP.

In some cases, a subject in vitro culture method increases ACAN gene expression, relative to β2M by at least about 25%, at least about 50%, at least about 2-fold, at least about 2.5-fold, at least about 3-fold, at least about 4-fold, at least about 5-fold, at least about 10-fold, or more than 10-fold, compared with ACAN gene expression in chondrocytes cultured in serum-free culture medium in the absence of a TGFβ superfamily protein and/or a BMP.

Gene expression can be determined using any of a variety of well-known methods, which include, e.g., quantitative polymerase chain reaction (qPCR) to determine the level of an mRNA product in a cell. Such methods can entail the use of nucleic acid primer pairs that specifically amplify a particular mRNA (or a cDNA copy of a particular mRNA), such as an aggrecan mRNA, a type 2 collagen mRNA, a Sox9 mRNA, and the like. Gene expression can also be determined by detecting a polypeptide product, using any of a variety of well-known methods, such as immunological methods, including, e.g., enzyme-linked immunosorbent assay (ELISA), immunoprecipitation assay, a Western blot assay, and the like. Antibody specific for the polypeptide product (e.g., aggrecan, collagen type 2, etc.) can be used.

Matrices

Chondrocytes generated as described above can be grown (cultured in vitro) without scaffold support to create a three-dimensional tissue for cartilage repair and/or bone formation. Alternatively, chondrocytes generated using a method of the present disclosure can be implanted in vivo in combination with suitable biodegradable, polymeric matrix or hydrogel to form new cartilage tissue and/or induce bone formation. Thus, the present disclosure provides a chondrocyte/matrix composition (or a hypertrophic cartilage/matrix composition; or a permanent cartilage/matrix composition), which composition is suitable for in vivo implantation into a treatment site in an individual. The composition can also be referred to as an "implant." The matrix can be provided with a binding agent that enables the implant to form a gel-like implant, a semi-solid implant, or a solid implant. Macromolecules included in the matrix (also referred to herein as a "scaffold") can include polypeptides, proteoglycans, polysaccharides, glycosaminoglycans, synthetic polymers, and the like. In certain embodiments, the matrix is a hydrogel. In certain embodiments, the matrix is a semi-interpenetrating network hydrogel.

For example, a matrix (also referred to as a "biocompatible substrate") is a material that is suitable for implantation into a subject. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate can provide the supportive framework that allows cells to attach to it and grow on it. Cells can also be suspended within the matrix.

Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

A subject chondrocyte/matrix composition can further comprise one or more additional components, where suitable additional components include, e.g., a growth factor; an antioxidant; an angiogenic factor; a nutritional transporter (e.g., transferrin); a polyamine (e.g., glutathione, spermidine, etc.); an antibiotic; and the like.

The cell density in a subject chondrocyte/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous, or can be molded to a shape that is suitable for a particular implantation site. The matrix can be in the form of a sheet, a cylinder, a sphere, etc. A matrix can also be provided in a shape that provides natural contours of a body part, e.g., a nose or nose part, an ear or ear part, a meniscus, etc.

Suitable matrices (scaffolds) include, but are not limited to, matrices comprising photopolymerizable components; matrices comprising fibrin glue components (e.g., thrombin and fibrinogen); alginates, including modified alginates; agarose; and collagen matrices.

Suitable matrices include those that form a hydrogel. The term "hydrogel" as used herein refers to a hydrophilic cross-linked polymer capable of containing a large volume fraction of water. For example, a hydrogel can contain more than about 70%, more than about 75%, more than about 80%, more than about 85%, or more than about 90% water on a volume/volume basis. When a hydrophilic polymer is formed in situ (e.g., in vivo), it can acquire water from its environment or from solutions used to create the hydrogel.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like. Suitable hydrogels include those described in U.S. Pat. No. 8,142,808.

A matrix can include a glycosaminoglycan (e.g., a polysaccharide comprising a basal structure containing an amino sugar and uronic acid or galactose). Suitable glycosaminoglycans include, but are not limited to, hyaluronic acid, chondroitin, chondroitin sulfate, dermatan sulfate, keratan sulfate, heparin, and heparan sulfate.

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "cellulose" includes cellulose and cellulose derivatives; similarly, "dextran" includes dextran and dextran derivatives thereof. In certain embodiments, the hydrophilic polymer is a poly(ethylene glycol).

Examples of materials that can be used to form a hydrogel include modified alginates. Alginate is a carbohydrate polymer isolated from seaweed, which can be crosslinked to form a hydrogel by exposure to a divalent cation such as calcium. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel, which are derivatized with hydrophobic, water-labile chains, e.g., oligomers of epsilon-caprolactone. The hydrophobic interactions induce gelation.

In some embodiments, a matrix component comprises a moiety comprising an arginine-glycine-aspartic acid (RGD) peptide covalently linked to another component. For example, an alginate can comprise a covalently linked moiety comprising an RGD peptide.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates. Polysaccharides which gel in the presence of monovalent cations form hydrogels upon exposure, for example, to a solution comprising physiological levels of sodium. Hydrogel precursor solutions also may be osmotically adjusted with a nonionic compound, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives can also be used. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from commercial sources.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., Obstetrics & Gynecology, vol. 77, pp. 48-52 (1991); and Steinleitner et al., Fertility and Sterility, vol. 57, pp. 305-308 (1992). Other materials which may be utilized include proteins such as fibrin, collagen, and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as within a few seconds.

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. In some cases, the negatively charged ions contain more than one carboxylate, sulfonate or phosphate group.

Exemplary anions for cross-linking of the polymers to form a hydrogel are monovalent, divalent or trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable membrane. Examples of materials that can be used include polymers having basic reactive groups such as amine or imine groups, e.g., having a molecular weight of between 3,000 daltons and 100,000 daltons, where exemplary polymers include polyethylenimine and polylysine. These are commercially available. An exemplary polycation is poly(L-lysine); examples of synthetic polyamines include polyethyleneimine, poly(vinylamine), and poly(allyl amine). Also suitable for use are naturally-occurring polycations such as chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically cross-linkable groups. Methods for modifying hydrophilic polymers to include these groups are well known to those of skill in the art.

Suitable polymers include natural polymers, semisynthetic polymers, and synthetic polymers. Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly (methacrylic acid)-t butyl ester, polytetrafluoroethylene, polyperfluoropropylene, poly N-vinyl carbazole, poly(m-ethyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid) or poly(L-lactide); poly(e-caprolactone); poly(ethylene glycol) (PEG); a derivatized PEG, poly(ethylene glycol) dimethacrylate (PEGDA); poly(lactide-co-glycolide); poly(hydroxybutyrate); poly(hydroxybutyrate-co-valerate); polydioxanone; polyorthoester; polyanhydride; polyethylene terephthalate (PET); polyethylene oxide (PEO), e.g crosslinkable PEO, non-crosslinkable PEO; poly(glycolic acid) (PGA); poly(D,L-lactide) (PDLL); poly(L-Lactide)(PLL); copolymers of PGA, PDLA, and/or PLA; poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers.

Suitable polymers for inclusion in a hydrogel include, but are not limited to, poly(N-isopropylacrylamide); poly(N-isopropylacrylamide-co-acrylic acid); hyaluronic acid or hyaluronate; crosslinked hyaluronic acid or hyaluronate; PHEMA; or copolymers p(NIPAAm)-based sIPNs and other hydrogel sIPNs (semi-interpenetrating networks).

In some embodiments, the hydrogel is a temperature-sensitive hydrogel. In some embodiments, a temperature-sensitive hydrogel is a polyacrylic acid or derivative thereof, e.g., poly (N-isopropylacrylamide) gel, and the increase in temperature causes the hydrogel to contract, thereby forcing the active agent out of the hydrogel. Alternatively, the temperature-sensitive hydrogel is an interpenetrating hydrogel network of poly(acrylamide) and poly(acrylic acid), and the increase in temperature causes the hydrogel to swell. The temperature required for triggering release of an active agent from the hydrogel is generally about normal body temperature, e.g., about 37° C.

Non-limiting examples of suitable matrix materials are PEGDA and PET, e.g., a scaffold that includes PEGDA and PET; and a sIPN network hydrogel, e.g., a sIPS network hydrogel comprising a non-crosslinkable PEO. For example, a scaffold comprising PEGDA and PET at a ratio of 30:70 provides for good chondrocyte matrix synthesis with sufficient mechanical properties and cell viability.

Suitable matrix components include collagen; a collagen derivative; a methylated collagen; a combination of a collagen or a derivative thereof and a fibrinogen; a combination of a collagen or a derivative thereof and a thrombin; a combination of (a) a collagen or a derivative thereof; (b) a fibrinogen; and (c) a thrombin; a combination of a methylated collagen and a poly(ethylene glycol) or a derivative thereof; atelopeptidic collagen telopeptide collagen cross-linked collagen; and the like.

Suitable matrix components include fibrin glue components such as fibrinogen and thrombin. For example, a matrix component can include a fibrinogen component comprising fibrinogen; and a thrombin component comprising thrombin. The fibrinogen component can further include aprotinin, a fibrinolysis inhibitor. The thrombin component can further include $CaCl_2$. The ratio of fibrinogen to thrombin can range from about 0.5:1 to about 2:1, e.g., from about 0.5:1 to about 1:1, from about 1:1 to about 1.5:1, or from about 1.5:1 to about 2:1.

Suitable matrix components include co-polymers of poly(ethylene glycol) of different molecular weights. For example, a matrix component can include a first PEG polymer of an average molecular weight in the range of from about 2,000 daltons (Da) to about 10,000 Da; and a second PEG polymer of an average molecular weight in the range of from about 10,000 Da to about 50,000 Da. The first and/or the second PEG polymer can be modified with a glycosaminoglycan, e.g., chondroitin sulfate, heparan sulfate, hyaluronic acid, etc.

An exemplary PEG gel comprises a nucleophilic "8-arm" octomer (PEG-NH$_2$, MW 20 kDa) and a "2-arm" amine-specific electrophilic dimer (SPA-PEG-SPA, MW 3.4 kDa), and is available from Shearwater Corporation, Huntsville, Ala. The addition-elimination polymerization reaction results in a nitrogen-carbon peptide-like linkage, resulting in a stable polymer whose rate of polymerization increases with pH and gel concentration.

Suitable polymers include synthetic polymers that comprise a photopolymerizable moiety. Suitable polymers include, e.g., water-soluble synthetic polymers including, but not limited to, poly(ethylene oxide) (PEO), poly(ethylene glycol) (PEG), poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers, provided that the conjugate is water soluble. Exemplary photopolymerizable moieties are acrylates, diacrylates, oligoacrylates, methacrylates, dimethacrylates, oligomethoacrylates, or other biologically acceptable photopolymerizable groups.

A synthetic polymer comprising one or more photopolymerizable moieties can be crosslinked via photopolymerization to one or more polysaccharides that are modified with one or more suitable photopolymerization moieties. Suitable polysaccharides include, e.g., alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan. For example, a polysaccharide can be modified by the addition of carbon-carbon double or triple bond-containing moieties, including acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups.

Initiation of polymerization is accomplished by irradiation with light at a wavelength of between about 200 nm-700 nm, e.g., in the long wavelength ultraviolet range or visible range, e.g., 320 nm or higher, or from about 376 nm to about 514 nm. This light can be provided by any appropriate source able to generate the desired radiation, such as a mercury lamp, longwave ultraviolet (UV) lamp, He—Ne laser, or an argon ion laser, or through the use of fiber optics.

An example of a water soluble conjugate is a block copolymer of polyethylene glycol and polypropylene oxide, e.g., poly(ethylene glycol) (PEG) polymers that include one or more photopolymerizable moieties that are polymerizable by photoinitiation. For example, a suitable polymer is a PEG polymer that includes one or more polymerizable moieties that are polymerizable by free radical generation, e.g., using visible or long wavelength ultraviolet radiation. One exemplary photopolymerizable PEG polymer is PEG-diacrylate. A suitable PEG polymer has an average molecular weight in a range of from about 2000 daltons (Da) to about 20,000 Da, e.g., from about 2,000 Da to about 4,000 Da, from about 4,000 Da to about 7,000 Da, from about 7,000 Da to about 10,000 Da, from about 10,000 Da to about 20,000 Da, from about 20,000 Da to about 30,000 Da, or from about 30,000 Da to about 40,000 Da. The PEG polymer comprises one or more photopolymerizable moieties, as described above.

A non-limiting example of a suitable polysaccharide is a glycosaminoglycan (e.g., a chondroitin sulfate, a heparan sulfate, a hyaluronic acid, etc.). An example of a chondroitin sulfate is chondroitin-4-sulfate (CS-4) and chondroitin-6-sulfate (CS-6). In some cases, a combination of CS-4 and CS-6 is used. The CS-4/CS-6 mixture can include 10%-90% CS-4 and 10%-90% CS6, e.g., a CS-4/CS-6 mixture can comprise 10%-20% CS-4 and 80%-90% CS-6; 20%-30% CS-4 and 70%-80% CS-6; 30%-40% CS4 and 60%-70% CS-6; 40%-60% CS4 and 40%-60% CS-6; 70%-80% CS-4 and 20%-30% CS-6; or 80%-90% CS4 and 10%-20% CS-6. The chondroitin sulfate is modified with a moiety such as acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups. For example, the CS-4 and the CS-6 can comprise a methacrylate moiety.

Exemplary photopolymerizable polymers includes chondroitin sulfate and a poly(ethylene glycol) as described in, e.g., Varghese et al. (2008) *Matrix Biol.* 27:12-21; Wang et al. (2007) *Nat. Mater.* 6:385; Elisseeff (2008) *Nat. Mater.* 7:271; Hwang et al. (2007) *Methods Mol. Biol.* 407:351.

Implantation into a Treatment Site

The present disclosure provides treatment methods, involving introducing in vitro-produced hypertrophic cartilage (optionally within a matrix, as described above) into a treatment site in vivo. The present disclosure provides methods of enhancing bone formation, the method involving introducing in vitro-produced hypertrophic cartilage (optionally within a matrix, as described above) into a treatment site in vivo.

The present disclosure provides treatment methods, involving introducing in vitro-produced permanently cartilage (optionally within a matrix, as described above) into a treatment site in vivo. The present disclosure provides methods of replacing missing, diseased, or damaged cartilage, the method involving introducing in vitro-produced permanent cartilage (optionally within a matrix, as described above) into a treatment site in vivo.

Implanting Hypertrophic Cartilage

Hypertrophic cartilage produced in vitro as described above can be introduced into a treatment site in an individual. Implanting hypertrophic cartilage into a treatment site in an individual in need thereof can replace missing cartilage; and/or can replace damaged or diseased cartilage; and/or can enhance bone formation.

In some embodiments, a subject method comprises: a) generating hypertrophic cartilage in vitro according to a method of the present disclosure, as described above; and b) implanting the in vitro-generated hypertrophic cartilage into a treatment site in a mammalian subject. Implanting the in vitro-generated hypertrophic cartilage into a treatment site provides for treatment, where treatment includes, e.g., repairing cartilage defects; replacing disease or damaged cartilage; and replacing cartilage that is missing due to age-related degeneration, sports-related degeneration, or disease-related degeneration.

Hypertrophic cartilage produced in vitro using a method of the present disclosure can repair cartilage defects produced as a result of injury, disease, or aging. Defects due to injury that can be repaired using a subject method can be sports- or accident-related, and may involve only the superficial cartilage layer, or may include the underlying subchondral bone. Defects due to disease which can be repaired using the hypertrophic cartilage described herein include those resulting from osteoarthritis and rheumatoid arthritis. Whether from injury or disease, such defects may be in either mature or growth plate cartilage.

A treatment site can be at or near (proximal to) a site of cartilage defect (e.g., missing, diseased, or injured cartilage). In some embodiments, the defective cartilage (e.g., missing, diseased, or injured cartilage) is articular cartilage. Treatment sites include, but are not limited to, knees, shoulders, vertebral column (e.g., at or near an intervertebral disc), and the like. In some cases, treatment site is a joint.

Hypertrophic cartilage produced in vitro using a method of the present disclosure can be introduced into (e.g., implanted into) a treatment site in an individual using any known method. Such methods include, e.g., injection directly into a treatment site; and surgical placement of the cartilage into a treatment site.

As discussed above, hypertrophic cartilage produced by a subject method is useful for replacing or regenerating cartilage in vivo, e.g., in an individual in need of cartilage replacement and/or regeneration. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a taxation of a joint by a torn ligament, mis-alignment of joints, bone fracture, or by hereditary disease. Hypertrophic cartilage produced by a subject method is also useful for remodeling cartilage matrix, such as in plastic or reconstructive surgery, as well as in periodontal surgery. Hypertrophic cartilage produced by a subject method can be used in conjunction with a reparative procedure, e.g., surgical repair of a meniscus, ligament, or cartilage.

In some instances, a hypertrophic cartilage composition will include one or more scaffold components that are photopolymerizable. In such instances, a subject treatment method can involve: a) introducing a subject hypertrophic cartilage composition into a treatment site in an individual; and b) exposing the introduced composition to a wavelength of light for such a time as to effect polymerization of the scaffold components.

In some instances a subject hypertrophic cartilage composition will include two components that, when mixed, will form a fibrin glue. In such instances, a subject treatment method can involve: a) admixing a first composition comprising thrombin with a second composition comprising fibrinogen, where one of the compositions also includes a subject hypertrophic cartilage composition, where the mixing results in a cartilage production admixture composition; and b) introducing the admixture composition into a treatment site in an individual. The time that elapses between the admixing and the introducing steps can be less than about 5 minutes.

A subject hypertrophic cartilage composition can be introduced into an individual in need thereof to regenerate cartilage of a diarthroidal joint, such as a knee, an ankle, an elbow, a hip, a wrist, a knuckle of a finger, a knuckle of a toe, or a temporomandibular joint. The treatment can be directed to the meniscus of the joint, to the articular cartilage of the joint, or both. As another example, a subject hypertrophic cartilage composition can be used to treat a degenerative disorder of a knee, e.g., where the degenerative disorder is the result of traumatic injury (e.g., a sports injury or excessive wear) or osteoarthritis.

As another example, a subject hypertrophic cartilage composition is introduced into an intervertebral disc, to treat degeneration of an intervertebral disc, and disorders resulting from degeneration of an intervertebral disc.

A subject hypertrophic cartilage composition is useful to enhance attachment of a prosthetic device implanted in an individual. A subject hypertrophic cartilage composition can also form a part of a prosthetic device, to be implanted into an individual. Prosthetic devices include, but are not limited to, an artificial meniscus, an artificial tendon, an artificial ligament, etc.

A subject hypertrophic cartilage composition can be used for remodeling cartilage matrix, such as in plastic or reconstructive surgery. For example, a subject hypertrophic cartilage composition can be used for remodeling cartilage in the external ear, in the nose, and the like.

A subject hypertrophic cartilage composition can be used to induce arthrodesis, e.g., in spinal applications. A subject hypertrophic cartilage composition can be used to replace damaged, diseased, or missing bone (e.g., to treat osteonecrosis). A subject hypertrophic cartilage composition can be used to replace the function of a growth place (physis), e.g., for use in pediatric orthopedics.

Enhancing Bone Formation

The present disclosure provides methods of enhancing bone formation, the method involving introducing in vitro-produced hypertrophic cartilage into a treatment site in vivo. In some embodiments, the method comprises: a) generating hypertrophic cartilage in vitro according to a method of the present disclosure, as described above; and b) implanting the in vitro-generated hypertrophic cartilage into a treatment site in the mammalian subject, where the implanted hypertrophic cartilage enhances formation of bone at the treatment.

A method of the present disclosure for enhancing bone formation can provide for an increase in bone volume and/or bone strength. A method of the present disclosure for enhancing bone formation is useful for repairing diseased or damaged bone; and for strengthening weakened bones (e.g., bones weakened due to immobility, insufficient calcium, aging, etc.); and for replacing missing bone. For example, a subject hypertrophic cartilage composition is useful for treating osteoporosis, for repairing bone fractures, and for carrying out bone reconstruction.

A treatment site can be at or near (proximal to) a site of bone deficiency, damage, or disease. Hypertrophic cartilage produced in vitro using a method of the present disclosure can be introduced into (e.g., implanted into) a treatment site in an individual using any known method. Such methods include, e.g., injection directly into a treatment site; and surgical placement of the cartilage into a treatment site.

Implanting Permanent Cartilage

Permanent cartilage produced in vitro as described above can be introduced into a treatment site in an individual. Implanting permanent cartilage into a treatment site in an individual in need thereof can replace missing cartilage, damaged cartilage, or diseased cartilage.

In some embodiments, a subject method comprises: a) generating permanent cartilage in vitro according to a method of the present disclosure, as described above; and b) implanting the in vitro-generated permanent cartilage into a treatment site in a mammalian subject. Implanting the in vitro-generated permanent cartilage into a treatment site provides for treatment, where treatment includes, e.g., repairing cartilage defects; replacing disease or damaged cartilage; and replacing cartilage that is missing due to age-related degeneration, sports-related degeneration, or disease-related degeneration.

Permanent cartilage produced in vitro using a method of the present disclosure can repair cartilage defects produced as a result of injury, disease, or aging. Defects due to injury that can be repaired using a subject method can be sports- or accident-related, and may involve only the superficial cartilage layer, or may include the underlying subchondral bone. Defects due to disease which can be repaired using the permanent cartilage described herein include those resulting from osteoarthritis and rheumatoid arthritis. Whether from injury or disease, such defects may be in either mature or growth plate cartilage.

A treatment site can be at or near (proximal to) a site of cartilage defect (e.g., missing, diseased, or injured cartilage). In some embodiments, the defective cartilage (e.g., missing, diseased, or injured cartilage) is articular cartilage. Treatment sites include, but are not limited to, knees, shoulders, vertebral column (e.g., at or near an intervertebral disc), and the like. In some cases, treatment site is a joint.

Permanent cartilage produced in vitro using a method of the present disclosure can be introduced into (e.g., implanted into) a treatment site in an individual using any known method. Such methods include, e.g., injection directly into a treatment site; and surgical placement of the cartilage into a treatment site. Permanent cartilage produced in vitro using a method of the present disclosure can be introduced intra-articularly.

As discussed above, permanent cartilage produced by a subject method is useful for replacing or regenerating cartilage in vivo, e.g., in an individual in need of cartilage replacement and/or regeneration. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a taxation of a joint by a torn ligament, mis-alignment of joints, bone fracture, or by hereditary disease. Permanent cartilage produced by a subject method is also useful for remodeling cartilage matrix, such as in plastic or reconstructive surgery, as well as in periodontal surgery. Permanent cartilage produced by a subject method can be used in conjunction with a reparative procedure, e.g., surgical repair of a meniscus, ligament, or cartilage.

In some instances, a permanent cartilage composition will include one or more scaffold components that are photopolymerizable. In such instances, a subject treatment method can involve: a) introducing a subject permanent cartilage composition into a treatment site in an individual; and b) exposing the introduced composition to a wavelength of light for such a time as to effect polymerization of the scaffold components.

In some instances a subject permanent cartilage composition will include two components that, when mixed, will form a fibrin glue. In such instances, a subject treatment method can involve: a) admixing a first composition comprising thrombin with a second composition comprising fibrinogen, where one of the compositions also includes a subject permanent cartilage composition, where the mixing results in a cartilage production admixture composition; and b) introducing the admixture composition into a treatment site in an individual. The time that elapses between the admixing and the introducing steps can be less than about 5 minutes.

A subject permanent cartilage composition can be introduced into an individual in need thereof to regenerate cartilage of a diarthroidal joint, such as a knee, an ankle, an elbow, a hip, a wrist, a knuckle of a finger, a knuckle of a toe, or a temporomandibular joint. The treatment can be directed to the meniscus of the joint, to the articular cartilage of the joint, or both. As another example, a subject permanent cartilage composition can be used to treat a degenerative disorder of a knee, e.g., where the degenerative disorder is the result of traumatic injury (e.g., a sports injury or excessive wear) or osteoarthritis.

As another example, a subject permanent cartilage composition is introduced into an intervertebral disc, to treat degeneration of an intervertebral disc, and disorders resulting from degeneration of an intervertebral disc.

A subject permanent cartilage composition is useful to enhance attachment of a prosthetic device implanted in an individual. A subject permanent cartilage composition can also form a part of a prosthetic device, to be implanted into an individual. Prosthetic devices include, but are not limited to, an artificial meniscus, an artificial tendon, an artificial ligament, etc.

A subject permanent cartilage composition can be used for remodeling cartilage matrix, such as in plastic or reconstructive surgery. For example, a subject permanent cartilage composition can be used for remodeling cartilage in the external ear, in the nose, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Generation of Hypertrophic Cartilage and Mineralized Bone

Culture in a Novel, Chemically-Defined, Serum-Free Media Enhances Chondrocyte Proliferation Compared to Culture in Standard, Serum-Containing Media.

Primary bovine articular chondrocytes were grown in serum-free or standard, serum-containing media. Cells were passaged at 90% confluence. Cumulative cell expansion was determined (FIG. 1). Culture in the serum-free condition led to much faster proliferation than culture in serum-containing media (13,700 fold expansion at 16 days compared to 40 fold expansion at 26 days).

FIG. 1: Comparison of chondrocyte expansion in serum-free versus serum-containing media.

Expansion in Serum-Free Media Maintains Cartilage-Gene Expression Better than Expansion in Serum-Containing Media.

Chondrocytes were cultured until passage 7 in serum-free or serum-containing media. They were then grown in pellet culture for an additional week, which enhances cartilage differentiation. Real-time PCR (qPCR) was then used to evaluate expression of the cartilage-related genes aggrecan (ACAN), type II collagen (Col 2), and Sox9. Serum-free conditions led to significantly higher expression (p<0.05) of ACAN and Col 2 (FIG. 2).

Figure 2:
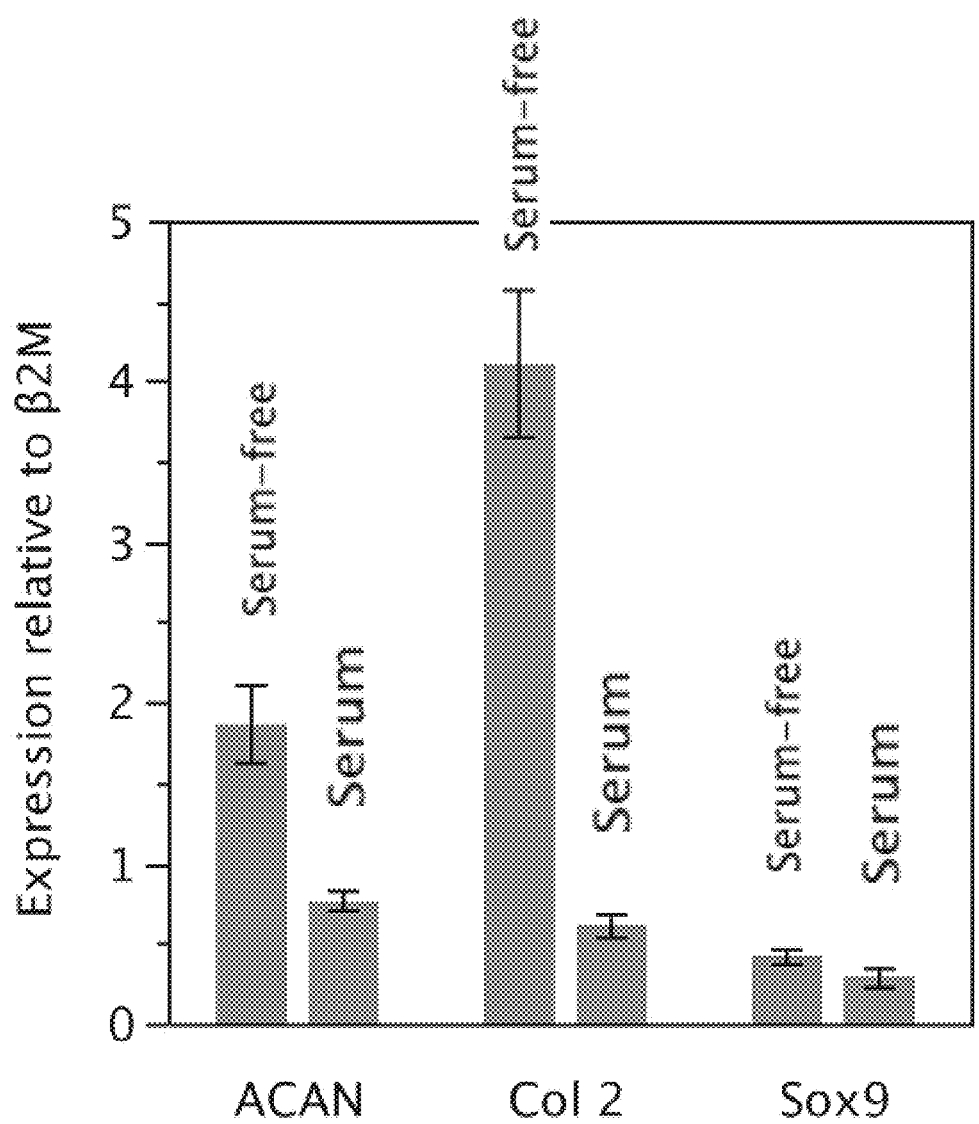
FIG. 2 depicts gene expression in chondrocytes expanded in serum-free culture conditions.

FIG. 2: Expansion of chondrocyte numbers in serum-free conditions maintains cartilaginous gene expression. Expression levels relative to the reference gene beta-2 microglobulin are shown.

TGF-β Superfamily Members Enhance Chondrogenesis of Chondrocytes Expanded in Serum-Free Conditions.

Figure 3:
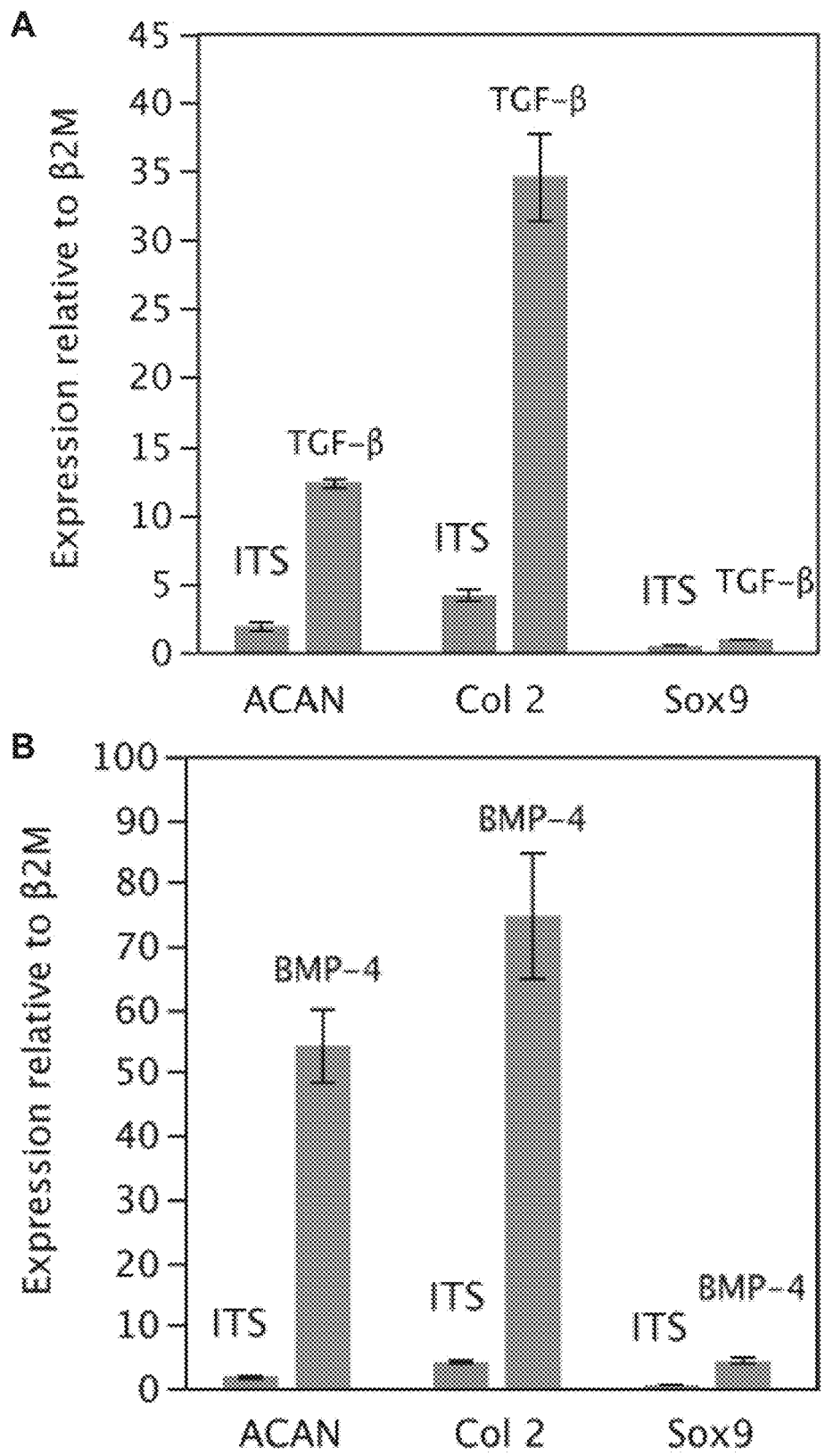
FIG. 3 depicts chondrogenic gene expression in chondrocytes cultured in medium including transforming growth factor-beta 1 (TGF-β1) or bone morphogenic protein-4 (BMP4).

Chondrocytes were expanded under serum-free conditions to passage 7 and subsequently grown in pellet culture. Pellets were treated with 1) TGF-β1, 2) Bone morphogenetic protein 4 (BMP-4), or 3) no additional treatment (control or ITS). Cells treated with TGF-β superfamily members expressed significantly more (p<0.05) ACAN, Col 2, and Sox9 (FIG. 3). Histology with safranin-O staining also showed that TGF-β and BMP treatment led to tissues that closely resembled native cartilage, with cells in lacunae and intense staining for proteoglycans (red staining) (FIG. 4). The BMP-4 treated chondrocytes assumed a hypertrophic morphology, with cells within large lacunae.

FIG. 3: Treatment of passaged chondrocytes with TGF-β1 or BMP-4 enhances chondrogenic gene expression. "ITS" indicates control cells.

FIG. 4: Treatment of passaged chondrocytes with TGF-β1 or BMP-3 leads to tissues that resemble native articular cartilage with intense safranin-O staining.

Implantation of Hypertrophic Pellets in Animals (Mice) Leads to the Formation of Bone.

Hypertrophic chondrocyte pellets derived arising from either BMP-4 treatment or combined BMP-4 and TGF-β treatment were implanted into subcutaneous pouches in mice. After 4 weeks, the pellets were harvested and the formation of mineralized tissue was assessed with microCT and histology (Von Kossa Staining). Results of both of these showed formation of tissues with characteristics consistent with bone (FIG. 5). When pellets treated with BMP-4 and parathyroid hormone-related peptide where implanted into mice, they maintained an appearance consistent with articular cartilage, with no formation of bone.

FIG. 5. Hypertrophic cartilage pellets stimulate bone formation when implanted in vivo. Chondrocyte pellets were grown under hypertrophic conditions and then implanted into mice. After 4 weeks, microCT analysis (left panel) shows formation of abundant mineralized tissue. Histology and Von Kossa staining shows mineralized tissue (black staining; right panel) with the appearance of bone.

Example 2: In Vitro Pre-Treatment of Passaged Chondrocytes can be Used to Control Endochondral Ossification when Implanted In Vivo Passaging of chondrocytes in vitro enhances the ability of these cells to form mineralized tissues during subsequent in vivo implantation.

Figure 13:
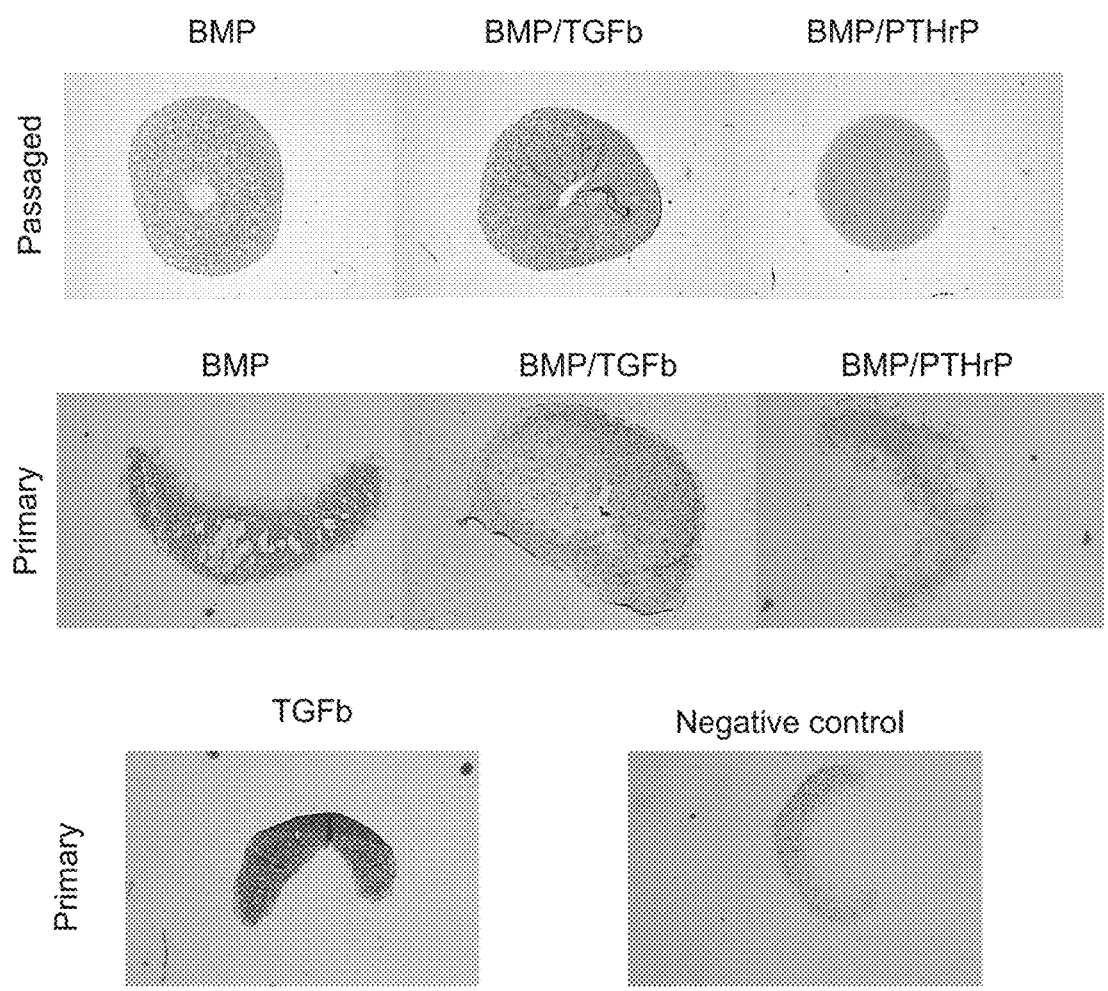
FIG. 13 depicts primary and passaged bovine articular chondrocytes that have been grown with the indicated treatments in vitro. Staining is with safranin-O for sulfated glycosaminoglycans.
Figure 15:
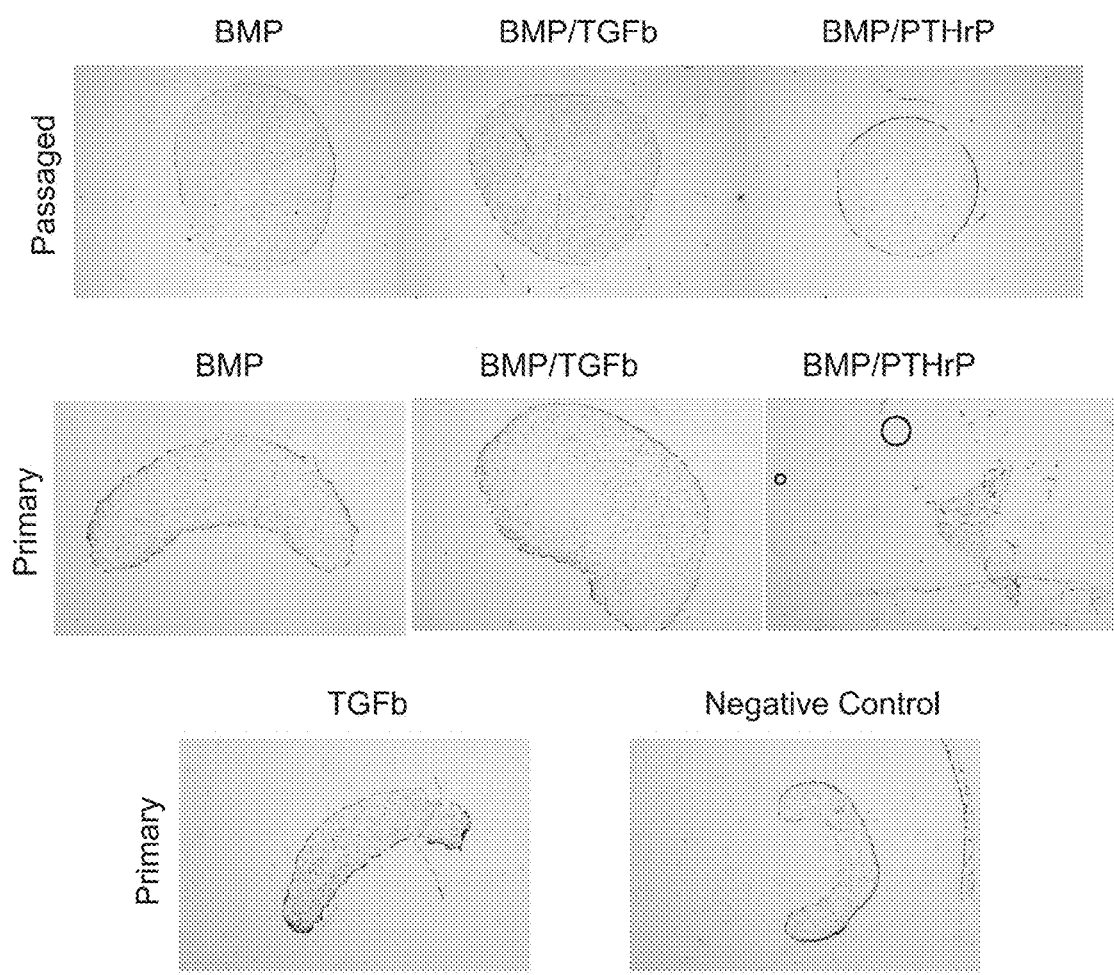
FIG. 15 depicts primary and passaged bovine articular chondrocytes grown in vitro under the indicated conditions and stained for mineralization using Von Kossa stain.
Figure 16:
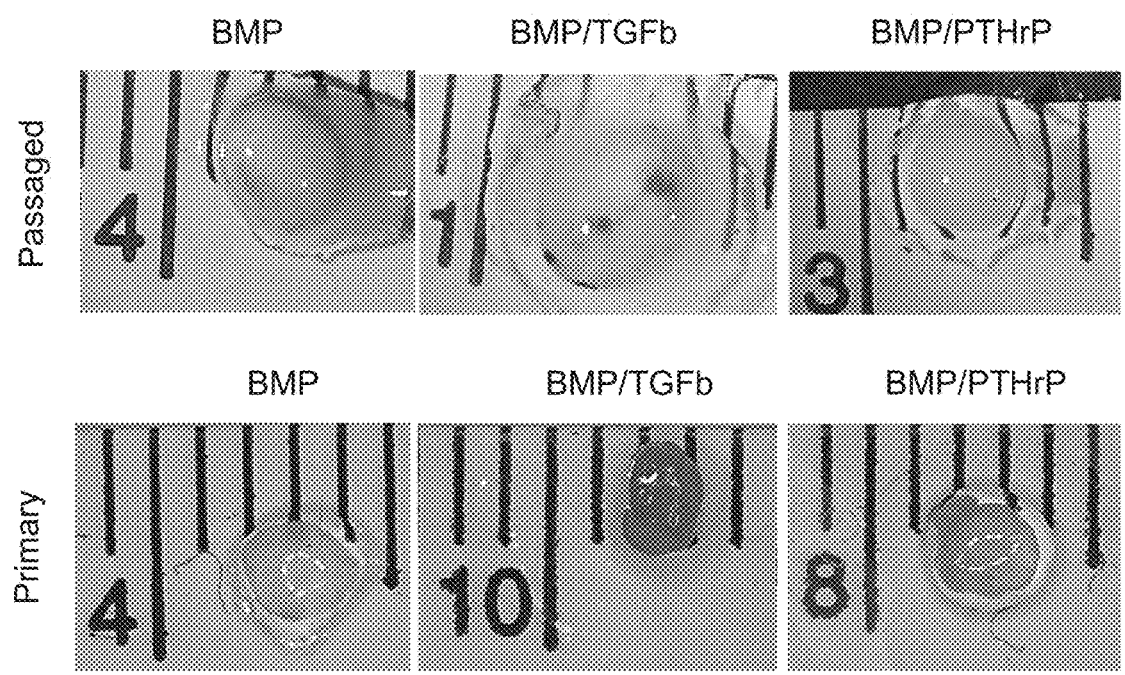
FIG. 16 depicts gross vascularization of primary and passaged bovine articular chondrocytes grown in vitro under the indicated conditions and then grown in vivo in murine subcutaneous pouches.
Figure 17:
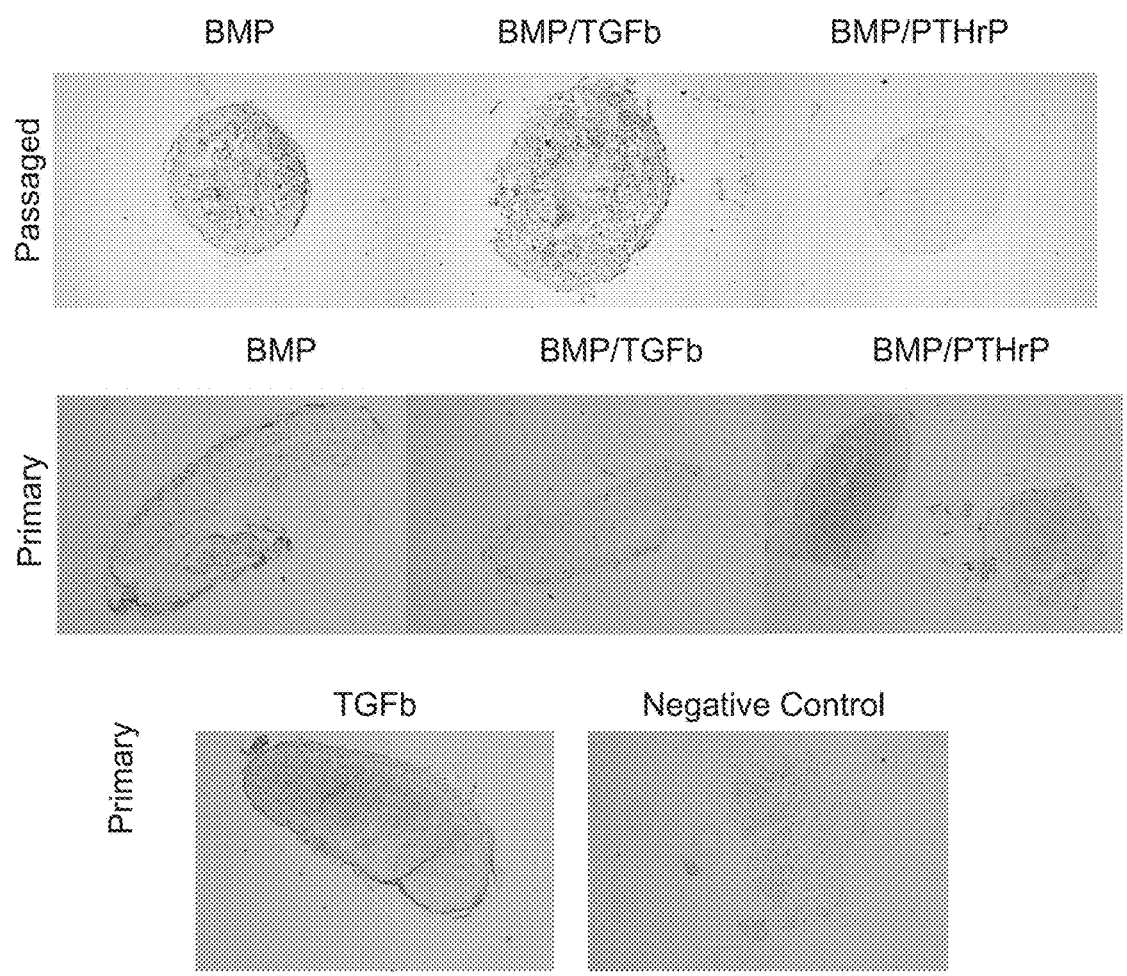
FIG. 17 depicts primary and passaged bovine articular chondrocytes grown in vitro under the indicated conditions and then grown in vivo in murine subcutaneous pouches. Samples are stained with safranin-O for glycosaminoglycan accumulation.
Figure 18:
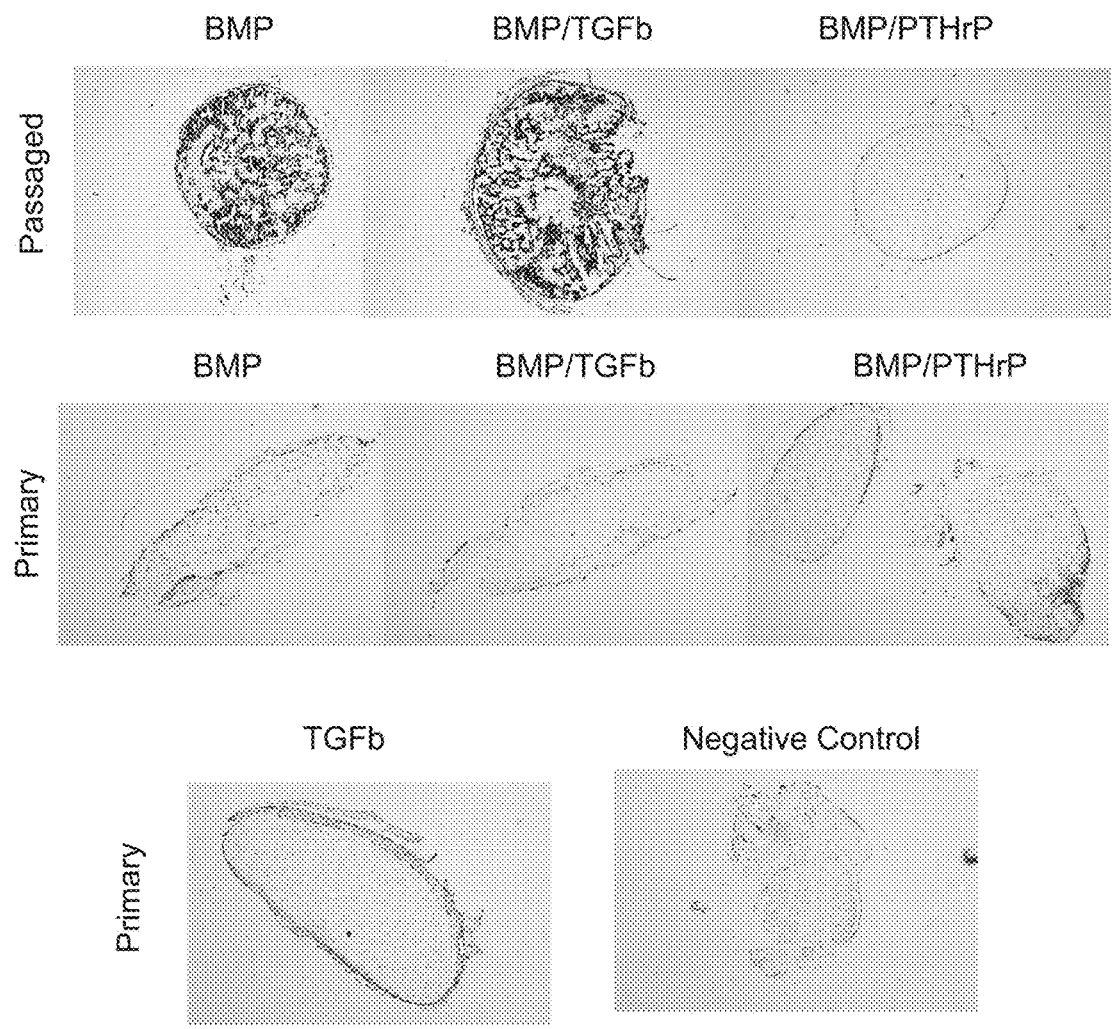
FIG. 18 depicts primary and passaged bovine articular chondrocytes grown in vitro under the indicated conditions and then grown in vivo in murine subcutaneous pouches. Samples are stained with Von Kossa stain to show mineralization.

Passaged and primary bovine articular chondrocytes were grown in pellet culture. Samples were treated for three days, then maintained in insulin-transferrin-sodium selenite media for a total of 28 days. A portion of these were harvested for histological analysis (FIGS. 13 and 15). The remaining pellets were implanted subcutaneously into nude mice (immune-compromised) and grown for another 28 days (FIGS. 16-18). The mice were then sacrificed and the pellets were harvested for histological analysis. Saffranin-O staining (FIG. 13 and FIG. 17) was used to visualize proteoglycan and Von Kossa staining (FIG. 15 and FIG. 18) was used to visualize calcium.

The results indicated that after in vitro treatment (prior to in vivo implantation)(FIGS. 13 and 15), passaged chondrocytes showed hypertrophy after treatment with BMP and BMP+TGFβ, but minimal to no hypertrophy when PTHrP was added along with BMP. Primary chondrocytes showed hypertrophy only when treated with BMP, but minimal to no hypertrophy when either TGFβ or PTHrP were added.

FIG. 13 depicts primary and passaged bovine articular chondrocytes that have been grown with the indicated treatments in vitro. Staining is with safranin-O for sulfated glycosaminoglycans.

Figure 14:
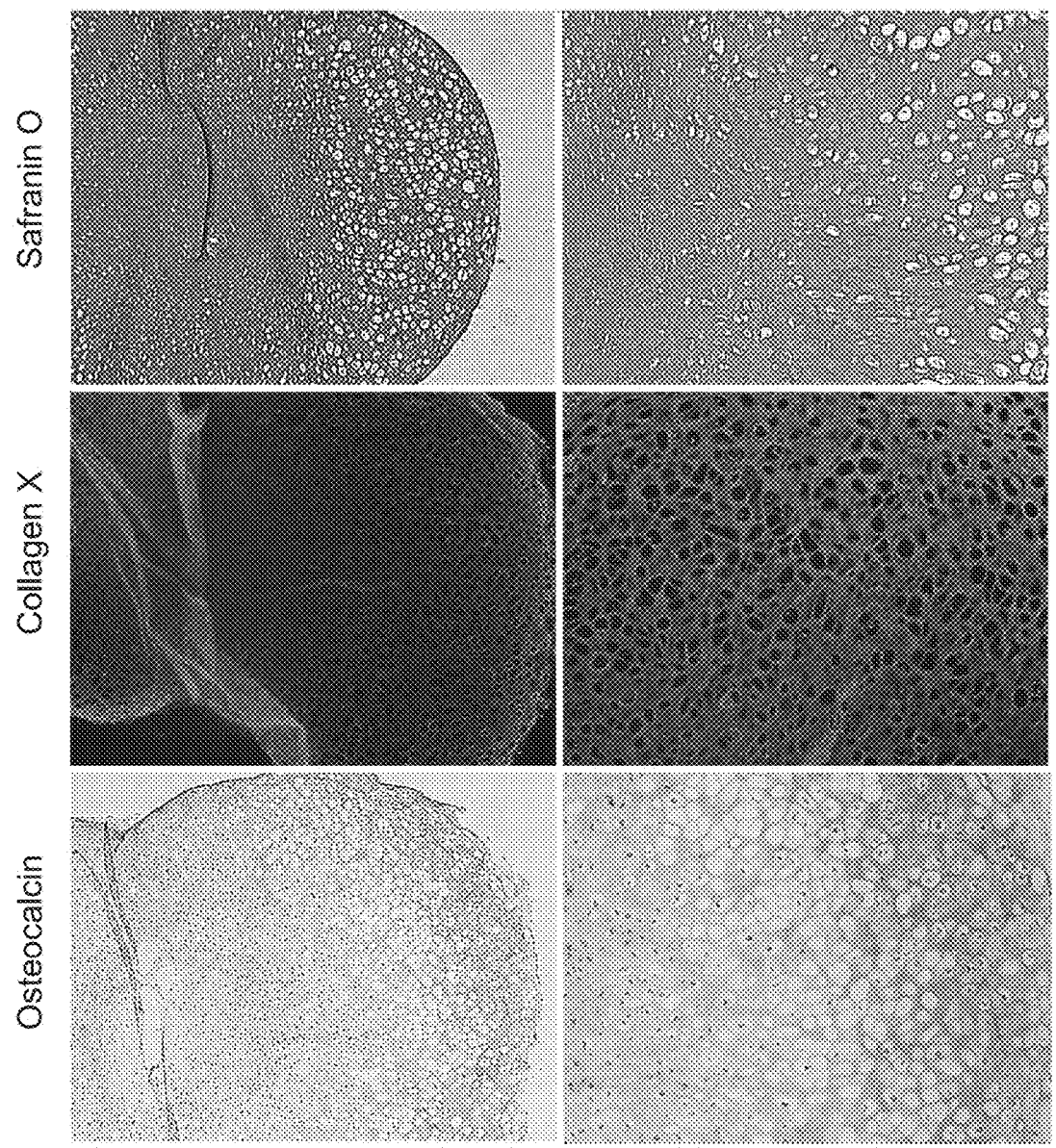
FIG. 14 depicts bovine articular chondrocytes grown in vitro with BMP and TGFβ and stained as indicated.

FIG. 14 depicts bovine articular chondrocytes grown in vitro with BMP and TGFβ and stained as indicated. These results indicate that TGFβ superfamily members cause articular chondrocytes to adopt a hypertrophic phenotype.

FIG. 15 depicts primary and passaged bovine articular chondrocytes grown in vitro under the indicated conditions and stained for mineralization using Von Kossa stain.

After in vivo implantation (FIGS. 16-18), passaged chondrocytes treated with BMP and BMP+TGFβ showed evidence of vascularization and calcium deposition, while samples treated with BMP+PTHrP did not. Passaged chondrocytes treated with BMP and BMP+TGFβ even lost their previous chondrocytic phenotype (it is also possible that they were replaced by tissues with a different phenotype after in vivo implantation). Primary chondrocytes treated with BMP and BMP+TGFβ seemed to have been absorbed into the mouse, while samples treated BMP+PTHrP maintained chondrocytic properties.

FIG. 16 depicts gross vascularization of primary and passaged bovine articular chondrocytes grown in vitro under the indicated conditions and then grown in vivo in murine subcutaneous pouches. Gross vascularization of the specimens (growth of blood vessels into the tissue) formed from passaged chondrocytes with TGFβ superfamily treatment is shown. Blood vessel formation is important for remodeling of hypertrophic cartilage into bone. Gross analysis of pellets harvested post implantation showed vascularization in passaged cells treated with BMP and BMP in conjunction with TGFβ. Minimal to no vascularization was observed either in passaged cells treated with BMP in conjunction with PTHrP; or in primary cells (i.e., cells that were not expanded prior to differentiation, i.e., only stage 2 was performed) regardless of treatment. The conclusion from this figure is that both stages are important for formation of functional hypertrophic cartilage.

FIG. 17 depicts primary and passaged bovine articular chondrocytes grown in vitro under the indicated conditions and then grown in vivo in murine subcutaneous pouches. Samples were stained with safranin-O for glycosaminoglycan accumulation.

FIG. 18 depicts primary and passaged bovine articular chondrocytes grown in vitro under the indicated conditions and then grown in vivo in murine subcutaneous pouches. Samples were stained with Von Kossa stain to show mineralization. Von Kossa staining showed calcification in passaged cells treated with BMP and BMP in conjunction with TGFβ. Minimal to no calcification was seen either in passaged cells treated with BMP in conjunction with PTHrP or in primary cells regardless of treatment. One conclusion is that such tissue (e.g., tissue that does not calcify) can be used for repairing permanent cartilage such as articular cartilage.

In vitro treatment with the biochemical factors above allowed for control of the cells without the caveats associated with biochemical usage in vivo. The effects of the biochemical factors persisted not only throughout the 25 day treatment in ITS media, but continued to persist through in vivo implantation.

In passaged chondrocytes, BMP treatment promoted hypertrophy and preconditioned the samples for vascularization and calcium deposition after implantation. The addition of TGFβ enhanced the effect while the addition of PTHrP suppressed it. Different combinations of these factors will allow for precise control over endochondral ossification with only one treatment in vitro.

These effects were not observed when using primary chondrocytes. The addition of BMP and TGFβ neither promoted vascularization and calcium deposition after implantation, nor maintained a cartilaginous phenotype. This may be due to BMP and TGFβ not persisting in primary chondrocytes. Addition of PTHrP did maintain the cartilaginous phenotype, which suggests that PTHrP plays a role in preserving the phenotype and preventing either ossification or integration.

It appears that passaging is not only non-detrimental, but beneficial. Because passaging chondrocytes causes de-differentiation, it is possible that de-differentiated chondrocytes become more malleable and therefore susceptible to the biochemical manipulation. Passaging also greatly increased the amount of usable cells derived from a given harvest. These data suggest that it may be possible to use chondrocytes collected from patients with osteoarthritis receiving arthroplasties. This allows for otherwise waste cartilage to be recycled, while bypassing the requirement for fresh cartilage and donor-site morbidity.

In conclusion, passaged chondrocytes can be conditioned to undergo endochondral ossification in a controlled manner. Conditioning is quick and done in vitro, while its effects persist and manifest in vivo.

Example 3: New Bone Formation Resulting from Induced Human Hypertrophic Cartilage Human articular chondrocytes from osteoarthritic joints were grown in vitro to expand cell numbers (ie passaging), and then grown with BMP and TGFβ in vitro. Samples were then grown in vivo in murine subcutaneous pouches. FIG. 19 depicts micro computed tomography (microCT) images of bone formation resulting from implantation of human induced hypertrophic cartilage. MicroCT analysis shows bone formation. Left panel shows a cross sectional image. Right panel shows a three dimensional image.

Figure 20:
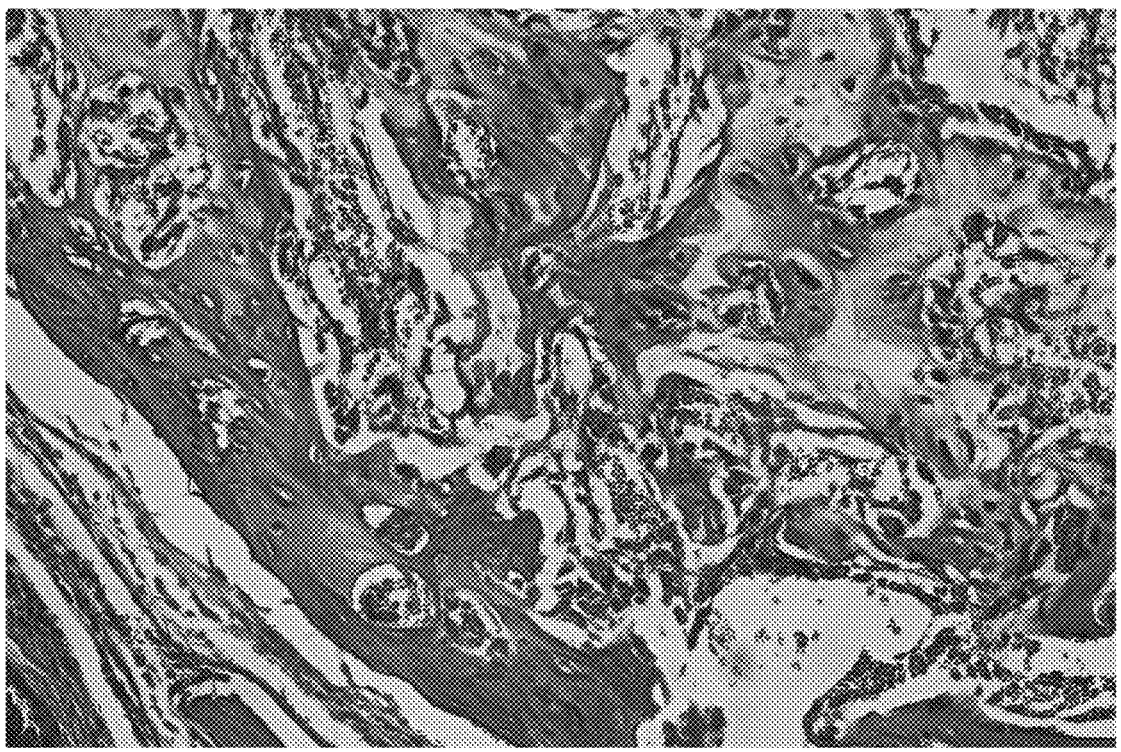
FIG. 20 depicts Trichrome staining of new bone formation resulting from induced human hypertrophic cartilage.

Human articular chondrocytes from the femoral resections of total knee replacements were isolated and subjected to the two-step process for induced hypertrophy. The induced hypertrophic cartilage was subsequently implanted into tibial defects in nude mice. After four weeks in vivo, the tissues were harvested and assessed histologically for bone formation. Trichrome staining shows replacement of the implanted cartilage with vascularized bone (dark blue regions) (FIG. 20). FIG. 20 depicts Trichrome staining of new bone formation resulting from induced human hypertrophic cartilage.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method of generating hypertrophic cartilage in vitro, the method comprising:
   a) culturing in a first liquid medium in vitro a starting population of chondrocytes, wherein the first liquid medium is serum free and comprises a transforming growth factor-β, (TGFβ) isoform wherein said culturing provides for an at least 50-fold increase in the number of chondrocytes over the number of chondrocytes in the starting population, thereby generating an expanded chondrocyte population; and
   b) culturing the expanded chondrocyte in vitro in a second liquid medium, wherein the second liquid medium is serum free and comprises a bone morphogenetic protein (BMP) isoform and optionally a transforming growth factor-β (TGFβ) isoform, wherein aggrecan and type II collagen expression is greater when the chondrocytes are expanded and cultured in the first and second liquid medium instead of serum containing medium; and said culturing in the second liquid medium results in production of hypertrophic cartilage.

2. The method of claim 1, wherein the TGFβ isoform comprises an amino acid sequence having at least 95% amino acid sequence identity to a TGF-β amino acid sequence set forth in any of SEQ ID NOs: 1-4 and 9.

3. The method of claim 1, wherein the TGFβ isoform is TGF-β1, TGF-β2, or TGF-β3.

4. The method of claim 1, wherein the BMP isoform comprises an amino acid sequence having at least 95% amino acid sequence identity to a BMP amino acid sequence set forth in any of SEQ ID NOs: 5 and 6.

5. The method of claim 1, wherein the BMP isoform is a BMP-4 isoform.

6. The method of claim 1, wherein the starting population of chondrocytes is substantially pure.

7. The method of claim 1, further comprising preparing a matrix composition comprising the cells.

8. A method of generating permanent cartilage in vitro, the method comprising
   a) culturing in a first liquid medium in vitro a starting population of chondrocytes, wherein the first liquid medium is serum free and comprises a transforming growth factor-β, (TGFβ) isoform, wherein said culturing provides for an at least 50-fold increase in the number of chondrocytes over the number of chondrocytes in the starting population, thereby generating an expanded chondrocyte population; and b) culturing the expanded chondrocyte in vitro in a second liquid medium, wherein the second liquid medium is serum free and comprises a bone morphogenetic protein (BMP) isoform and optionally a transforming growth factor-β (TGFβ) isoform, wherein the second liquid medium further includes a parathyroid hormone-related (PTHrP) isoform, wherein aggrecan and type II collagen expression is greater when the chondrocytes are expanded and cultured in the first and second liquid medium instead of serum containing medium; and said culturing in the second liquid medium results in production of permanent cartilage.

9. The method of claim 8, wherein the TGFβ isoform comprises an amino acid sequence having at least 95% amino acid sequence identity to a TGF-0 amino acid sequence set forth in any of SEQ ID NOs: 1-4 and 9.

10. The method of claim 8, wherein the TGFβ isoform is TGF-01, TGF-02, or TGF-03.

11. The method of claim 8, wherein the BMP isoform comprises an amino acid sequence having at least 95% amino acid sequence identity to a BMP amino acid sequence set forth in any of SEQ ID NOs: 5 and 6.

12. The method of claim 8, wherein the BMP isoform is a BMP-4 isoform.

13. The method of claim 8, wherein the PTHrP isoform comprises an amino acid sequence having at least 95% amino acid sequence identity to a PTHrP amino acid sequence set forth in any of SEQ ID NOs: 8 and 10.

14. The method of claim 8, wherein the starting population of chondrocytes is substantially pure.

\* \* \* \* \*

UNITED STATES PATENT AND TRADEMARK OFFICE
CERTIFICATE OF CORRECTION

PATENT NO. : 10,047,343 B2
APPLICATION NO. : 14/599324
DATED : August 14, 2018
INVENTOR(S) : Alfred Kuo Page 1 of 1

It is certified that error appears in the above-identified patent and that said Letters Patent is hereby corrected as shown below:

In the Claims

Claim 9, Line 15, "TGF-0" should read --TGF-$\beta$--;

Claim 10, Line 18, "TGF-01" should read --TGF-$\beta$1--;

Claim 10, Line 18, "TGF-02" should read --TGF-$\beta$2--; and

Claim 10, Line 18, "TGF-03" should read --TGF-$\beta$3--.

Signed and Sealed this
Sixth Day of November, 2018

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 390
<212> TYPE: PRT
<213> ORGANISM: Homo sapiens

<400> SEQUENCE: 1

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
```

115                 120                 125
His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 2
<211> LENGTH: 390
<212> TYPE: PRT
<213> ORGANISM: Mus musculus

<400> SEQUENCE: 2

Met Pro Pro Ser Gly Leu Arg Leu Leu Pro Leu Leu Pro Leu Pro Pro
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
                85                  90                  95

```
Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
        115                 120                 125

His Ser Ile Tyr Met Phe Phe Asn Thr Ser Asp Ile Arg Glu Ala Val
    130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
    210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ser Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 3
<211> LENGTH: 414
<212> TYPE: PRT
<213> ORGANISM: Homo sapiens

<400> SEQUENCE: 3

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80
```

```
Lys Ala Ser Arg Arg Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220

His Cys Pro Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Met Leu Leu Pro Ser
        275                 280                 285

Tyr Arg Leu Glu Ser Gln Gln Thr Asn Arg Arg Lys Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
        355                 360                 365

Thr Ile Asn Pro Glu Ala Ser Ala Ser Pro Cys Cys Val Ser Gln Asp
    370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410

<210> SEQ ID NO 4
<211> LENGTH: 414
<212> TYPE: PRT
<213> ORGANISM: Mus musculus

<400> SEQUENCE: 4

Met His Tyr Cys Val Leu Ser Thr Phe Leu Leu Leu His Leu Val Pro
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
```

```
            35                  40                  45
Lys Leu Thr Ser Pro Pro Glu Asp Tyr Pro Glu Pro Asp Glu Val Pro
 50                  55                  60

Pro Glu Val Ile Ser Ile Tyr Asn Ser Thr Arg Asp Leu Leu Gln Glu
 65                  70                  75                  80

Lys Ala Ser Arg Ala Ala Ala Cys Glu Arg Glu Arg Ser Asp Glu
                 85                  90                  95

Glu Tyr Tyr Ala Lys Glu Val Tyr Lys Ile Asp Met Pro Ser His Leu
                100                 105                 110

Pro Ser Glu Asn Ala Ile Pro Pro Thr Phe Tyr Arg Pro Tyr Phe Arg
            115                 120                 125

Ile Val Arg Phe Asp Val Ser Thr Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Ala Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val Gln
        195                 200                 205

Glu Trp Leu His His Lys Asp Arg Asn Leu Gly Phe Lys Ile Ser Leu
210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Ala Ser Gly Asp Gln Lys Thr Ile Lys Ser Thr Arg Lys
            260                 265                 270

Lys Thr Ser Gly Lys Thr Pro His Leu Leu Leu Met Leu Leu Pro Ser
        275                 280                 285

Tyr Arg Leu Glu Ser Gln Gln Ser Ser Arg Arg Lys Lys Arg Ala Leu
        290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Thr Lys Val Leu Ser Leu Tyr Asn
        355                 360                 365

Thr Ile Asn Pro Glu Ala Ser Ala Ser Pro Cys Cys Val Ser Gln Asp
370                 375                 380

Leu Glu Pro Leu Thr Ile Leu Tyr Tyr Ile Gly Asn Thr Pro Lys Ile
385                 390                 395                 400

Glu Gln Leu Ser Asn Met Ile Val Lys Ser Cys Lys Cys Ser
                405                 410

<210> SEQ ID NO 5
<211> LENGTH: 408
<212> TYPE: PRT
<213> ORGANISM: Homo sapiens

<400> SEQUENCE: 5
```

-continued

```
Met Ile Pro Gly Asn Arg Met Leu Met Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu
                85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
                115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
                195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
                275                 280                 285

Arg Ala Lys Arg Ser Pro Lys His His Ser Gln Arg Ala Arg Lys Lys
                290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
                340                 345                 350

Asn His Ala Ile Val Gln Thr Leu Val Asn Ser Val Asn Ser Ser Ile
                355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Leu Lys Asn Tyr Gln Glu Met
385                 390                 395                 400

Val Val Glu Gly Cys Gly Cys Arg
                405
```

```
<210> SEQ ID NO 6
<211> LENGTH: 408
<212> TYPE: PRT
<213> ORGANISM: Mus musculus

<400> SEQUENCE: 6

Met Ile Pro Gly Asn Arg Met Leu Met Val Val Leu Leu Cys Gln Val
 1               5                  10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Pro Gln Pro Ser Lys Ser Ala Val Ile Pro
 65                  70                  75                  80

Asp Tyr Met Arg Asp Leu Tyr Arg Leu Gln Ser Gly Glu Glu Glu
                85                  90                  95

Glu Glu Gln Ser Gln Gly Thr Gly Leu Glu Tyr Pro Glu Arg Pro Ala
            100                 105                 110

Ser Arg Ala Asn Thr Val Arg Ser Phe His His Glu Glu His Leu Glu
        115                 120                 125

Asn Ile Pro Gly Thr Ser Glu Ser Ser Ala Phe Arg Phe Leu Phe Asn
    130                 135                 140

Leu Ser Ser Ile Pro Glu Asn Glu Val Ile Ser Ser Ala Glu Leu Arg
145                 150                 155                 160

Leu Phe Arg Glu Gln Val Asp Gln Gly Pro Asp Trp Glu Gln Gly Phe
                165                 170                 175

His Arg Ile Asn Ile Tyr Glu Val Met Lys Pro Pro Ala Glu Met Val
            180                 185                 190

Pro Gly His Leu Ile Thr Arg Leu Leu Asp Thr Arg Leu Val His His
        195                 200                 205

Asn Val Thr Arg Trp Glu Thr Phe Asp Val Ser Pro Ala Val Leu Arg
    210                 215                 220

Trp Thr Arg Glu Lys Gln Pro Asn Tyr Gly Leu Ala Ile Glu Val Thr
225                 230                 235                 240

His Leu His Gln Thr Arg Thr His Gln Gly Gln His Val Arg Ile Ser
                245                 250                 255

Arg Ser Leu Pro Gln Gly Ser Gly Asp Trp Ala Gln Leu Arg Pro Leu
            260                 265                 270

Leu Val Thr Phe Gly His Asp Gly Arg Gly His Thr Leu Thr Arg Arg
        275                 280                 285

Arg Ala Lys Arg Ser Pro Lys His His Pro Gln Arg Ser Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380
```

```
Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 7
<211> LENGTH: 115
<212> TYPE: PRT
<213> ORGANISM: Homo sapiens

<400> SEQUENCE: 7

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
                100                 105                 110

Lys Ser Gln
        115

<210> SEQ ID NO 8
<211> LENGTH: 175
<212> TYPE: PRT
<213> ORGANISM: Homo sapiens

<400> SEQUENCE: 8

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
                20                  25                  30

Arg Leu Lys Arg Ala Val Ser Glu His Gln Leu Leu His Asp Lys Gly
            35                  40                  45

Lys Ser Ile Gln Asp Leu Arg Arg Arg Phe Phe Leu His His Leu Ile
        50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
                100                 105                 110

Thr Tyr Lys Glu Gln Pro Leu Lys Thr Pro Gly Lys Lys Lys Lys Gly
            115                 120                 125

Lys Pro Gly Lys Arg Lys Glu Gln Glu Lys Lys Arg Arg Thr Arg
        130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg
                165                 170                 175
```

```
<210> SEQ ID NO 9
<211> LENGTH: 412
<212> TYPE: PRT
<213> ORGANISM: Homo sapiens

<400> SEQUENCE: 9

Met Lys Met His Leu Gln Arg Ala Leu Val Val Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
                35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
                115                 120                 125

Ser Lys Val Phe Arg Phe Asn Val Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
                260                 265                 270

His His Asn Pro His Leu Ile Leu Met Met Ile Pro Pro His Arg Leu
                275                 280                 285

Asp Asn Pro Gly Gln Gly Gln Arg Lys Lys Arg Ala Leu Asp Thr
                290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
370                 375                 380
```

```
Pro Leu Thr Ile Leu Tyr Tyr Val Gly Arg Thr Pro Lys Val Glu Gln
385                 390                 395                 400

Leu Ser Asn Met Val Lys Ser Cys Lys Cys Ser
            405                 410

<210> SEQ ID NO 10
<211> LENGTH: 177
<212> TYPE: PRT
<213> ORGANISM: Homo sapiens

<400> SEQUENCE: 10

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
                100                 105                 110

Thr Tyr Lys Glu Gln Pro Leu Lys Thr Pro Gly Lys Lys Lys Lys Gly
            115                 120                 125

Lys Pro Gly Lys Arg Lys Glu Gln Glu Lys Lys Lys Arg Arg Thr Arg
        130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His
```